United States Patent
Yu et al.

(10) Patent No.: US 9,433,667 B2
(45) Date of Patent: *Sep. 6, 2016

(54) CANCER VACCINES AND VACCINATION METHODS

(75) Inventors: John S. Yu, Los Angeles, CA (US); Gentao Liu, Los Angeles, CA (US); Keith L. Black, Los Angeles, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 575 days.

This patent is subject to a terminal disclaimer.

(21) Appl. No.: 13/327,125

(22) Filed: Dec. 15, 2011

(65) Prior Publication Data

US 2012/0156232 A1 Jun. 21, 2012

Related U.S. Application Data

(62) Division of application No. 11/864,177, filed on Sep. 28, 2007, now Pat. No. 8,097,256.

(60) Provisional application No. 60/827,260, filed on Sep. 28, 2006.

(51) Int. Cl.
*A61K 39/00* (2006.01)
*C12N 5/0784* (2010.01)
*A61K 35/12* (2015.01)

(52) U.S. Cl.
CPC ......... *A61K 39/0011* (2013.01); *C12N 5/0639* (2013.01); *A61K 2035/124* (2013.01); *A61K 2039/5154* (2013.01); *C12N 2501/22* (2013.01); *C12N 2501/23* (2013.01); *C12N 2501/25* (2013.01)

(58) Field of Classification Search
None
See application file for complete search history.

(56) References Cited

U.S. PATENT DOCUMENTS

| | | | |
|---|---|---|---|
| 4,690,915 A | 9/1987 | Rosenberg | |
| 4,844,893 A | 7/1989 | Honsik et al. | |
| 5,635,363 A | 6/1997 | Altman et al. | |
| 5,643,786 A | 7/1997 | Cohen et al. | |
| 5,788,963 A | 8/1998 | Murphy et al. | |
| 5,831,016 A | 11/1998 | Wang et al. | |
| 5,843,448 A | 12/1998 | Chen et al. | |
| 5,843,633 A | 12/1998 | Yin et al. | |
| 5,844,075 A * | 12/1998 | Kawakami et al. ......... 530/326 | |
| 5,846,538 A | 12/1998 | Cheever et al. | |
| 5,849,589 A | 12/1998 | Tedder et al. | |
| 5,851,756 A | 12/1998 | Steinman et al. | |
| 5,869,445 A | 2/1999 | Cheever et al. | |
| 5,876,712 A | 3/1999 | Cheever et al. | |
| 5,925,729 A | 7/1999 | Boon et al. | |
| 5,994,126 A | 11/1999 | Steinman et al. | |
| 6,010,905 A | 1/2000 | Cohen et al. | |
| 6,015,567 A | 1/2000 | Hudziak et al. | |
| 6,037,135 A | 3/2000 | Kubo et al. | |
| 6,077,519 A | 6/2000 | Storkus et al. | |
| 6,248,329 B1 | 6/2001 | Chandrashekar et al. | |
| 6,300,090 B1 | 10/2001 | Steinman et al. | |
| 6,455,678 B1 | 9/2002 | Yin et al. | |
| 6,458,585 B1 | 10/2002 | Vachula et al. | |
| 6,479,286 B1 | 11/2002 | Nelson et al. | |
| 6,482,405 B1 | 11/2002 | Tahara et al. | |
| 6,514,942 B1 | 2/2003 | Ioannides et al. | |
| 6,537,560 B1 | 3/2003 | Kawakami et al. | |
| 6,566,395 B1 | 5/2003 | Moran | |
| 6,632,459 B2 | 10/2003 | Graus et al. | |
| 6,984,522 B2 | 1/2006 | Clarke et al. | |
| 7,115,360 B2 | 10/2006 | Clarke et al. | |
| 7,186,409 B2 | 3/2007 | Snyder et al. | |
| 7,204,982 B2 | 4/2007 | Liau | |
| 7,247,480 B2 | 7/2007 | Waldmann et al. | |
| 7,311,916 B2 | 12/2007 | Wild et al. | |
| 7,338,929 B2 | 3/2008 | Debinski et al. | |
| 7,368,531 B2 | 5/2008 | Rosen et al. | |
| 7,402,314 B2 | 7/2008 | Sherman et al. | |
| 7,504,490 B1 | 3/2009 | Weinstock et al. | |
| 7,842,466 B1 | 11/2010 | Kim et al. | |
| 8,097,256 B2 | 1/2012 | Yu et al. | |
| 8,129,184 B2 | 3/2012 | Yu | |
| 8,168,586 B1 | 5/2012 | Fang et al. | |
| 8,383,768 B2 | 2/2013 | Singh et al. | |
| 8,604,167 B2 | 12/2013 | Singh et al. | |
| 8,871,211 B2 | 10/2014 | Yu et al. | |
| 2002/0034819 A1 | 3/2002 | Smith et al. | |
| 2002/0045261 A1 | 4/2002 | Snyder et al. | |
| 2002/0076707 A1 | 6/2002 | Mack et al. | |
| 2002/0115213 A1 | 8/2002 | Snyder et al. | |
| 2002/0119121 A1 | 8/2002 | Vitiello et al. | |
| 2002/0182194 A1 * | 12/2002 | Ju et al. .................... 424/93.21 |
| 2002/0192211 A1 | 12/2002 | Hudziak et al. | |
| 2003/0064916 A1 * | 4/2003 | Sherman .......................... 514/4 |
| 2003/0095955 A1 | 5/2003 | Noessner et al. | |

(Continued)

FOREIGN PATENT DOCUMENTS

| CA | 2 500 715 | 4/2015 |
|---|---|---|
| WO | WO 89/06692 | 7/1989 |

(Continued)

OTHER PUBLICATIONS

Yu et al Cancer Res. 61:842-847, 2001, Yu 2001.*
Yu et al , Cancer Res. 64:4973-79, 2004, Yu 2004.*
Liu et al J Immunother 27:220-226, 2004.*
Al-Hajj et al., "Prospective identification of tumorigenic breast cancer cells," Proc. Natl. Acad. Sci. USA, 7:3983-88 (2003).
Altaner, "Glioblastoma and stem cells," Neoplasma, 55:369-374 (2008).
Beier et al., "CD133+ and CD133− glioblastoma-derived cancer stem cells show differential growth characteristics and molecular profiles," Cancer Res., 67:4010-15 (2007).
Bjerkvig et al., "Opinion: the origin of the cancer stem cell: current controversies and new insights," Nat. Rev. Cancer, 11:899-904 (2005).
Boman et al., "Cancer stem cells: a step toward the cure," J. Clin. Oncol., 26:2795-99 (2008).
Brown et al., "Recognition and killing of brain tumor stem-like initiating cells by CD8+ cytolytic T cells," Cancer Res., 69:8886-93 (2009).
Carpentier et al., Neuron, 64: 79-92 (2009).
Drukker et al., "Characterization of the expression of MHC proteins in human embryonic stem cells," Proc. Natl. Acad. Sci. USA, 99:9864-69 (2002).
Communication for Application No. EP 07843269.7, dated Feb. 2, 2011, 9 pages.
Gearhart, Science, 282: 1061-1062 (1998).

(Continued)

*Primary Examiner* — Lei Yao

(74) *Attorney, Agent, or Firm* — Fish & Richardson P.C.

(57) ABSTRACT

Methods and compositions for treating cancers (e.g., neural cancers) by dendritic cell vaccination are provided herein.

10 Claims, 7 Drawing Sheets

(56) References Cited

U.S. PATENT DOCUMENTS

| | | |
|---|---|---|
| 2003/0185823 A1 | 10/2003 | Lum et al. |
| 2003/0190682 A1 | 10/2003 | Law et al. |
| 2003/0202963 A1 | 10/2003 | Crystal et al. |
| 2003/0204052 A1 | 10/2003 | Herrmann et al. |
| 2003/0204071 A1 | 10/2003 | Moore et al. |
| 2004/0057935 A1 | 3/2004 | Yu et al. |
| 2004/0072246 A1 | 4/2004 | Martin et al. |
| 2004/0121946 A9 | 6/2004 | Fikes et al. |
| 2004/0197903 A1 | 10/2004 | Pestano |
| 2004/0203143 A1 | 10/2004 | Tjoa et al. |
| 2005/0059151 A1 | 3/2005 | Bosch |
| 2005/0119198 A1 | 6/2005 | Carmeliet et al. |
| 2005/0169897 A1 | 8/2005 | Snyder et al. |
| 2006/0003323 A1 | 1/2006 | Alsobrook et al. |
| 2006/0204509 A1 | 9/2006 | Harty et al. |
| 2007/0020297 A1 | 1/2007 | Wheeler et al. |
| 2007/0098776 A1 | 5/2007 | Fikes et al. |
| 2007/0167375 A1 | 7/2007 | Okada et al. |
| 2008/0076904 A1 | 3/2008 | Cheever et al. |
| 2008/0107668 A1 | 5/2008 | Philip et al. |
| 2008/0131448 A1 | 6/2008 | Debinski et al. |
| 2008/0166374 A1 | 7/2008 | Debinski et al. |
| 2008/0199484 A1 | 8/2008 | Yu et al. |
| 2008/0206286 A1 | 8/2008 | Yu |
| 2008/0311141 A1 | 12/2008 | Yu et al. |
| 2008/0311142 A1 | 12/2008 | Yu et al. |
| 2009/0093052 A1 | 4/2009 | Yin et al. |
| 2009/0110702 A1 | 4/2009 | Wu et al. |
| 2009/0305418 A1 | 12/2009 | Moriarty et al. |
| 2010/0040637 A1 | 2/2010 | Van Orden et al. |
| 2010/0135975 A1 | 6/2010 | Yu et al. |
| 2010/0310643 A1 | 12/2010 | Singh et al. |
| 2012/0052080 A1 | 3/2012 | Okada et al. |
| 2012/0189664 A1 | 7/2012 | Yu |
| 2012/0231030 A1 | 9/2012 | Derouazi et al. |
| 2013/0115279 A1 | 5/2013 | Singh et al. |
| 2013/0183328 A1 | 7/2013 | Yu et al. |
| 2013/0183378 A1 | 7/2013 | Yu et al. |
| 2014/0234350 A1 | 8/2014 | Yu et al. |
| 2014/0234351 A1 | 8/2014 | Yu et al. |

FOREIGN PATENT DOCUMENTS

| | | |
|---|---|---|
| WO | WO 92/20356 | 11/1992 |
| WO | WO 94/26293 | 11/1994 |
| WO | WO 95/21862 | 8/1995 |
| WO | WO 96/18409 | 6/1996 |
| WO | WO 00/24778 | 5/2000 |
| WO | WO 00/38730 | 7/2000 |
| WO | WO 00/66713 | 11/2000 |
| WO | WO 01/08636 | 2/2001 |
| WO | WO 01/41741 | 6/2001 |
| WO | WO 01/58479 | 8/2001 |
| WO | WO 01/68148 | 9/2001 |
| WO | WO 02/068474 | 9/2002 |
| WO | WO 03/010301 | 2/2003 |
| WO | WO 03/014335 | 2/2003 |
| WO | WO 03/035004 | 5/2003 |
| WO | WO 03/066097 | 8/2003 |
| WO | WO 03/092717 | 11/2003 |
| WO | WO 2005/028505 | 3/2005 |
| WO | WO 2005/037995 | 4/2005 |
| WO | WO 2005/043155 | 5/2005 |
| WO | WO 2005/079581 | 9/2005 |
| WO | WO 2006/034334 | 3/2006 |
| WO | WO2006034334 * | 3/2006 |
| WO | WO 2007/062138 | 5/2007 |
| WO | WO 2008/039874 | 4/2008 |
| WO | WO 2008/039969 | 4/2008 |
| WO | WO 2008/039974 | 4/2008 |
| WO | WO 2008/052740 | 5/2008 |
| WO | WO 2008/054716 | 5/2008 |
| WO | WO 2008/083949 | 7/2008 |
| WO | WO 2010/028066 | 3/2010 |
| WO | WO 2010/129895 | 11/2010 |
| WO | WO 2012/079000 | 6/2012 |

OTHER PUBLICATIONS

Geschwind et al., "A genetic analysis of neural progenitor differentiation," Neuron, 2:325-39 (2001).
Ghods et al., "Spheres isolated from 9L gliosarcoma rat cell line possess chemoresistant and aggressive cancer stem-like cells," Stem Cells, 7:1645-53 (2007).
Harizi et al., "Prostaglandin E2 modulates dendritic cell function via EP2 and EP4 receptor subytpes," J. Leukocyte Biol., 73:756-763 (2003).
Hemmati et al., "Cancerous stem cells can arise from pediatric brain tumors," Proc. Natl. Acad. Sci. USA, 25:15178-83 (2003).
Hirschmann-Jax et al., "A distinct 'side population' of cells with high drug efflux capacity in human tumor cells," Proc. Natl. Acad. Sci. USA, 39:14228-33 (2004).
Hori et al., "Neural progenitor cells lack immunogenecity and resist destruction as allografts," Stem Cells, 21:405-416 (2003).
International Search Report and Written Opinion of the International Searching Authority for PCT/US2007/79600, mailed on Mar. 27, 2008, 10 pages.
International Search Report and Written Opinion; PCT/US2014/16562; Jun. 3, 2014; 37 pp.
International Search Report and Written Opinion; PCT/US2014/16610; Jun. 5, 2014; 24 pp.
Koch et al., "Immune-privileged embryonic Swiss mouse STO and STO cell-derived progenitor cells: major histocompatibility complex and cell differentiation antigen expression patterns resemble those of human embryonic stem cell lines," Immunology, 119:98-115 (2006).
Lee et al., "Isolation of neural stem cells from the postnatal cerebellum," Nat. Neurosci., 6:723-729 (2005).
Li et al., "Human embryonic stem cells possess immune-privileged properties," Stem Cells, 22:448-456 (2004).
Mizrak et al., "CD133: molecule of the moment," J. Pathol., 214:3-9 (2008).
Neuzil et al., "Tumour-initiating cells vs. cancer 'stem' cells and CD133: what's in the name?" Biochem. Biophys. Res. Commun., 355:855-859 (2007).
O'Brien et al., "A human colon cancer cell capable of initiating tumour growth in immunodeficient mice," Nature, 7123:106-110 (2007).
Pellegatta et al., "Dendritic cell vaccines for cancer stem cells," Methods Mol. Biol., 568:233-247 (2009).
Pellegatta et al., "Neurospheres enriched in cancer stem-like cells are highly effective in eliciting a dendritic cell-mediated immune response against malignant gliomas," Cancer Res., 66:10247-52 (2006).
Reya et al., "Stem cells, cancer, and cancer stem cells," Nature, 6859:105-111 (2001).
Reynolds and Weiss, "Generation of neurons and astrocytes from isolated cells of the adult mammalian central nervous system," Science, 5052:1707-10 (1992).
Reynolds et al, "A multipotent EGF-responsive striatal embryonic progenitor cell produces neurons and astrocytes," J. Neurosci., 11:4565-74 (1992).
Sanai et al., "Neural stem cells and the origin of gliomas," N. Eng. J. Med., 8:811-822 (2005).
Singh et al., "Cancer stem cells in nervous tumors," Oncogene, 23:7267-73 (2004).
Singh et al., "Identification of human brain tumor initiating cells", Nature, 7015:396-401 (2004).
Steele et al., "The polycomb group proteins, BMI-1 and EZH2, are tumour-associated antigens," Br. J. Cancer 95:1202-11 (2006).
Tian et al., "Expression of immunoglobulin superfamily cell adhesion molecules on murine embryonic stem cells," Biol. Reprod., 57:561-568 (1997).
Tunici et al., "Brain tumor stem cells: new targets for clinical treatments?" Neurosurg. Focus, 4:E27 (2006).

(56) References Cited

OTHER PUBLICATIONS

Tunici et al., "Genetic alterations and in vivo tumorigenicity of neurospheres derived from an adult glioblastoma," Mol. Cancer, 3:25 (2004).
Wu et al., "Embryonic stem cells and their differentiated derivatives have fragile immune privilege but still represent novel targets of immune attack," Stem Cells, 26:1939-50 (2008).
Wu et al., "Expression of MHC I and NK ligands on human CD133+ glioma cells: possible targets of immunotherapy," J. Neurooncol., 83:121-131 (2007).
Xu et al., "Hedgehog signaling regulates brain tumor-initiating cell proliferation and portends shorter survival for patients with PTEN-coexpressing glioblastomas," Stem Cells, 26:3018-26 (2008).
Yamanaka et al.; 2003; British J. Can. vol. 89: 1172-79 (0006002).
Yin et al., "Expression and regulation of major histocompatibility complex on neural stem cells and their lineages," Stem Cells Dev., 17:53-65 (2008).
Yin et al., "AC133, a novel marker for human hematopoietic stem and progenitor cells," Blood, 12:5002-12 (1997).
Yu et al., "AC133-2, a novel isoform of human AC133 stem cell antigen," J. Biol. Chem., 23:20711-16 (2002).
Zabierowski and Herlyn, "Melanoma stem cells: the dark seed of melanoma," J. Clin. Oncol., 26:2890-94 (2008).
Zhou et al., "The ABC transporter Berp1/ABCG2 is expressed in a wide variety of stem cells and is a molecular determinant of the side-population phenotype," Nat. Med., 9:1028-34 (2001).
Zou et al., "Cancer initiating cells or cancer stem cells in the gastrointestinal tract and liver," J. Cell. Physiol., 217:598-604 (2008).
Ahmed et al.; "HER2-Specific T Cells Target Primary Glioblastoma Stem Cells and Induce Regression of Autologous Experimental Tumors"; Clin Cancer Res.; 16(2); 474-85.
European Patent Office Communication for European Application No. 09812172.6, mailed May 23, 2012, 5 pages.
Garcia-Hernandez et al., "Prostate Stem Cell Antigen Vaccination Induces a Long-term Protective Immune Response against Prostate Cancer in the Absence of Autoimmunity", Cancer Res., vol. 68, No. 3, (2008), pp. 861-869.
Hemmer et al., "Contribution of Individual Amino Acids Within MHC Molecule or Antigenic Peptide to TCR Ligand Potency," J. Immunol., 164:861-871 (2000).
International Preliminary Report on Patentability for App. Ser. No. PCT/US2010/034082, mailed Nov. 17, 2011, 5 pages.
International Preliminary Report on Patentability of International Application No. PCT/US2009/055759, issued Mar. 8, 2011 (mailed Mar. 17, 2011), 7 pages.
International Search Report and Written Opinion of International Application No. PCT/US2009/055759, mailed Jun. 28, 2010, 12 pages.
International Search Report and Written Opinion of International Application No. PCT/US2010/034082, mailed Feb. 22, 2011, 9 pages.
Kalinski et al., "Prostaglandin E2 induces the final maturation of IL-12 deficient CD1a+CD83+ dendritic cells: the levels of IL-12 are determined during the final dendritic cell maturation and are resistant to further modulation," J. Immunol, 161:2804-09 (1998).
Kimchi-Sarfaty et al., "A "Silent" Polymorphism in the MDR1 Gene Changes Substrate Specificity", Science, vol. 315, (2007), pp. 525-528 (Erratum, 1 page).
NCBI GenBank Accession No. NM_006017 (Jul. 13, 2008), 5 pages.
Nielsen et al., "Reliable prediction of T-cell epitopes using neural networks with novel sequence representations," Protein Sci., 12:1007-1017 (2003).
Ordonez et al.; "Value of Mesothelin Immunostaining in the Diagnosis of Mesothelioma"; Mod. Pathol., Mar. 2003; vol. 16, No. 3, pp. 192-197.
Parkhurst et al., "Improved Induction of Melanoma-Reactive CTL with Peptides from the Melanoma Antigen gp100 Modified at HLA-A*0201-Binding Residues," J. Immunol., 157:2539-2548 (1996).
Posnett et al., "A novel method for producing anti-peptide antibodies. Production of site-specific antibodies to the T cell antigen receptor beta-chain," J. Biol. Chem., 263:1719-25 (1988).
Smith et al., "CD133/prominin-1 is a potential therapeutic target for antibody-drug conjugates in hepatocellular and gastric cancers," Br. J. Cancer, 99:100-109 (2008).
USPTO Final Office Action in U.S. Appl. No. 12/552,945, mailed Aug. 16, 2012, 13 pages.
USPTO Non-Final Office Action in U.S. Appl. No. 12/552,945, mailed Mar. 12, 2012, 20 pages.
USPTO Non-Final Office Action in U.S. Appl. No. 12/776,200, mailed Apr. 18, 2012, 10 pages.
USPTO Non-Final Office Action in U.S. Appl. No. 12/776,200, mailed Aug. 7, 2012, 14 pages.
USPTO Final Office Action in U.S. Appl. No. 13/365,666, mailed Oct. 6, 2014, 14 pages.
USPTO Final Office Action in U.S. Appl. No. 12/552,945, mailed Oct. 22, 2014, 27 pages.
Van Der Burg et al., "Immunogenicity of Peptides Bound to MHC Class I Molecules Depends on the MHC-Peptide Complex Stability", J. Immunol., 156:3308-3314 (1996).
Zhang et al., "Extensively cross-reactive anti-HIV-1 neutralizing antibodies induced by gp140 immunization," PNAS 24:10193-10198 (2007).
USPTO Non-Final Office Action in U.S. Appl. No. 13/828,432, mailed Dec. 1, 2014 (12 pages).
Abdel-Wahab et al., "Human dendritic cells, pulsed with either melanoma tumor cell lysates or the gp100 peptide(280-288), induce pairs of T cell cultures with similar phenotype and lytic activity," Cell. Immunol., 186:63-74 (1998).
Akasaki et al., "Antitumor effect of immunizations with fusions of dendritic and glioma cells in a mouse brain tumor model," J. Immunother., 24:106-113 (2001).
Akasaki et al., "Dendritic cell-based immunotherapy for malignant gliomas," Expert Rev. Neurother., 5:497-508 (2005).
Akasaki et al., "Induction of a CD4+ T regulatory type 1 response by cyclooxygenase-2-overexpressing glioma," J. Immunol., 173:4352-59 (2004).
Akasaki et al., "T cell immunity in patients with malignant glioma: recent progress in dendritic cell-based immunotherapeutic approaches," Front. Biosci., 10:2908-21 (2005).
Borbulevych et al., "Increased immunogenicity of an anchor-modified tumor-associated antigen is due to the enhanced stability of the peptide/MHC complex: implications for vaccine design," J. Immunol., 174:4812-20 (2005).
Borras et al., "Findings on T cell specificity revealed by synthetic combinatorial libraries," J. Immunol. Methods, 267:79-97 (2002).
Bowles, Jr. et al., "Long-term remission of malignant brain tumors after intracranial infection: a report of four cases," Neurosurgery, 44:636-642 (1999).
Bullock et al., "Antigen density presented by dendritic cells in vivo differentially affects the number and avidity of primary, memory, and recall CD8+ T cells," J. Immunol., 170:1822-29 (2003).
Candido et al., "Local administration of dendritic cells inhibits established breast tumor growth: implications for apoptosis-inducing agents," Cancer Res., 61:228-236 (2001).
Casey et al., "Heat shock protein derived from a non-autologous tumour can be used as an anti-tumour vaccine," Immunology, 110:105-111 (2003).
Castelli et al., "Novel HLA-Cw8-restricted T cell epitopes derived from tyrosinase-related protein-2 and gp100 melanoma antigens," J. Immunol., 162:1739-48 (1999).
Castro et al., "Current and future strategies for the treatment of malignant brain tumors," Pharmacol. Ther., 98:71-108 (2003).
Chandler et al., "Long-term survival in patients with glioblastoma multiforme," Neurosurgery, 32:716-720 (1993).
Chen et al., "Identification of the *MAGE-1* gene product by monoclonal and polyclonal antibodies," Proc. Natl. Acad. Sci. USA, 91:1004-08 (1994).

(56) References Cited

OTHER PUBLICATIONS

Cho et al., "Recent advances of dendritic cells (DCs)-based immunotherapy for malignant gliomas," Cell Transplant., 18:977-983 (2009).
Curran et al., "Recursive partitioning analysis of prognostic factors in three radiation therapy oncology group malignant glioma trials," J. Natl. Cancer Inst., 85:704-710 (1993).
Czerniecki et al., "Targeting HER-2/neu in early breast cancer development using dendritic cells with staged interleukin-12 burst secretion," Cancer Res., 67:1842-52 (2007).
Debinsky, "Correspondence re: B. H. Joshi et al., Interluekin-13 Receptor α Chain: A Novel Tumor-associated Transmembrane Protein in Primary Explants of Human Malignant Gliomas. Cancer Res., 60: 1168-1172, 2000," Cancer Res., 61:5660 (2001).
Dietz, "Engineering dendritic cell grafts for clinical trials in cellular immunotherapy of cancer: example of chronic myelogenous leukemia," Croatian Med. J., 42:428-435 (2001).
Ehtesham et al., "Intratumoral dendritic cell vaccination elicits potent tumoricidal immunity against malignant glioma in rats," J. Immunother., 26:107-116 (2003).
Ehtesham et al., "Recent progress in immunotherapy for malignant glioma: treatment strategies and results from clinical trials," Cancer Control, 11:192-207 (2004).
Falk et al., "Allele-specific motifs revealed by sequencing of self-peptides eluted from MHC molecules," Nature, 351:290-296 (1991).
Friedman et al., "Temozolomide and treatment of malignant glioma," Clin. Cancer Res., 6:2585-97 (2000).
Galli et al., "Isolation and characterization of tumorigenic, stem-like neural precursors from human glioblastoma," Cancer Res., 64:7011-21 (2004).
Gatza et al., "Tumor cell lysate-pulsed dendritic cells are more effective than TCR Id protein vaccines for active immunotherapy of T cell lymphoma," J. Immunol., 169:5227-35 (2002).
Geiger et al., "Vaccination of pediatric solid tumor patients with tumor lysate-pulsed dendritic cells can expand specific T cells and mediate tumor regression," Cancer Res., 61:8513-19 (2001).
Gilboa et al., "Immunotherapy of cancer with dendritic-cell-based vaccines," Cancer Immunol. Immunother., 46:82-87 (1998).
Haas et al., "Cycloxygenase-2 inhibition augments the efficacy of a cancer vaccine," Clin. Cancer Res., 12:214-222 (2006).
Hahn et al., "Short-term dietary administration of celecoxib enhances the efficacy of tumor lysate-pulsed dendritic cell vaccines in treating murine breast cancer," Int. J. Cancer, 118:2220-31 (2006).
Harada et al., "Melanoma-reactive CD8+ T cells recognize a novel tumor antigen expressed in a wide variety of tumor types," J. Immunother., 24:323-333 (2001).
Haynes et al., "Molecular characterization of the B″ regulatory subunit gene family of Arabidopsis protein phosphatase 2A", Euro J. Biochem., vol. 260, (1999), pp. 127-136.
Heimberger et al., "Bone marrow-derived dendritic cells pulsed with tumor homogenate induce immunity against syngeneic intracerebral glioma," J. Neuroimmunol., 103:16-24 (2000).
Inoue et al., "Dendritic cells coinjected with tumor cells treated with an anticancer drug to induce tumor rejection," Surg. Today, 33:269-276 (2003).
Irvin et al., "T cells enhance stem-like properties and conditional malignancy in gliomas," PLoS One, 5;e10974 (2010).
Ji et al., "Glioma stem cell research for the development of immunotherapy," Neurosurg. Clin. N. Am., 21:159-66 (2010).
Joshi et al., "Interleulcin-13 receptor α chain: a novel tumor-associated transmembrane protein in primary explants of human malignant gliomas," Cancer Res., 60:1168-72 (2000).
Khong et al., "Pre-existing immunity to tyrosinase-related protein (TRP)-2, a new TRP-2 isoforrn, and the NY-ESO-1 melanoma antigen in a patient with a dramatic response to immunotherapy," J. Immunol, 168:951-956 (2002).
Kikuchi et al., "Results of a phase I clinical trial of vaccination of glioma patients with fusions of dendritic and glioma cells," Cancer Immunol. Immumother., 50:337-344 (2002).
Kikuchi et al., "Intratumoral injection of dendritic and irradiated glioma cells induces anti-tumor effects in a mouse brain tumor model," Cancer Immunol. Immumother., 51:424-430 (2002).
Knutson et al., "Technology evaluation: DCVax, Northwest Biotherapeutics," Curr. Opin. Mol. Ther., 4:403-407 (2002).
Kuby et al., Immunology, W. H. Freeman and Co., pp. 523-524 (1992).
La Rosa et al., "Enhanced immune activity of cytotoxic T-lymphocyte epitope analogs derived from positional scanning synthetic combinatorial libraries," Blood, 97:1776-86 (2001).
Lefranc, "Editorial: On the road to multi-modal and pluri-disciplinary treatment of glioblastomas," Acta Neurochir. (Wien), 151:109-112 (2009).
Lemmel et al., "Differential quantitative analysis of MHC ligands by mass spectrometry using stable isotope labeling," Nat. Biotechnol., 22:450-454 (2004).
Liau et al., "Treatment of intracranial gliomas with bone marrow-derived dendritic cells pulsed with tumor antigens," J. Neurosurg., 90:1115-24 (1999).
Liu et al., "Analysis of gene expression and chemoresistance of CD133+ cancer stem cells in glioblastoma," Mol. Cancer, 5:67 (2006).
Liu et al., "Chemoresistance of stem-like cells isolated from glioblastoma," Proc. Amer. Assoc. Cancer Res., 47:75, abstract #320 (2006).
Liu et al., "AIM-2: a novel tumor antigen is expressed and presented by human glioma cells," J. Immunother., 27:220-226 (2004).
Liu et al., "Cell-mediated immunotherapy: a new approach to the treatment of malignant glioma," Cancer Control, 10:138-147 (2003).
Liu et al., "Cytotoxic T cell targeting of TRP-2 sensitizes human malignant glioma to chemotherapy," Oncogene, 24:5226-34 (2005).
Liu et al., "HER-2, gp100, and MAGE-1 are expressed in human glioblastoma and recognized by cytotoxic T cells," Cancer Res., 64:4980-86 (2004).
Liu et al., "Molecular and functional analysis of tyrosinase-related protein (TRP)-2 as a cytotoxic T lymphocyte target in patients with malignant glioma," J. Immunother., 26:301-312 (2003).
Liu et al., "Sensitization of malignant glioma to chemotherapy through dendritic cell vaccination," Expert Rev. Vaccines, 5:233-247 (2006).
Liu et al., "Small interference RNA modulation of IL-10 in human monocyte-derived dendritic cells enhances the Th1 response," Eur. J. Immunol., 34:1680-87 (2004).
Liu and Yu, "Cancer vaccines: a novel strategy to sensitize malignant glioma to chemotherapy," Expert Rev. Neurother., 7:1235-37 (2007).
Lupetti et al., "Translation of a retained intron in tyrosinase-related protein (TRP) 2 mRNA generates a new cytotoxic T lymphocyte (CTL)-defined and shared human melanoma antigen not expressed in normal cells of the melanocytic lineage," J. Exp. Med., 188:1005-16 (1998).
Luptrawan et al., "Dendritic cell immunotherapy for malignant gliomas," Rev. Recent Clin, Trials, 3:10-21 (2008).
Lustgarten et al., "Identification of cross-reactive peptides using combinatorial libraries circumvents tolerance against Her-2/neu-immunodominant epitope," J. Immunol., 176:1796-1805 (2006).
Lynch et al., "Flt3 ligand induces tumor regression and antitumor immune responses in vivo," Nat. Med., 3:625-631 (1997).
Maitland and Collins, "Prostate cancer stem cells: a new target for therapy," J. Clin. Oncol., 26:2862-70 (2008).
Mammolenti et al., "Absence of major histocompatibility complex class I on neural stem cells does not permit natural killer cell killing and prevents recognition by alloreactive cytotoxic T lymphocytes in vitro," Stem Cells, 22:1101-10 (2004).
Mehta-Damani et al., "Generation of antigen-specific CD8+ CTLs from naive precursors," J. Immunol., 153:996-1003 (1994).
Mehta-Damani et al., "Generation of antigen-specific CD4+ T cell lines from naive precursors," Eur. J. Immunol., 5:1206-11 (1995).

(56) References Cited

OTHER PUBLICATIONS

Melcher et al., "Dendritic cells for the immunotherapy of cancer," Clin. Oncol., 14:185-192 (2002).
Merrick et al., "Autologous versus allogeneic peptide-pulsed dendritic cells for anti-tumour vaccination: expression of allogeneic MHC supports activation of antigen specific T cells, but impairs early naïve cytotoxic priming and anti-tumour therapy," Cancer Immunol. Immunother., 57:897-906 (2008).
Mi et al., "Induced apoptosis supports spread of adenovirus vectors in tumors," Hum. Gene Ther., 12:1343-52 (2001).
Ngo, J. et al., "Computational Complexity, Protein Structure Prediction and the Levinthal Paradox", (1994), The Protein Folding Problem and Tertiary Structure Prediction, Merz et al. (eds.), Birkhauser Boston: Boston, MA, pp. 433 and 492-495.
Nowak et al., "Synergy between chemotherapy and immunotherapy in the treatment of established murine solid tumors," Cancer Res., 63:4490-96 (2003).
Okada et al., "Bone marrow-derived dendritic cells pulsed with a tumor-specific peptide elicit effective anti-tumor immunity against intracranial neoplasms," Int J. Cancer, 78:196-201 (1998).
Okada et al., "Autologous glioma cell vaccine admixed with interleukin-4 gene transfected fibroblasts in the treatment of recurrent glioblastoma: preliminary observations in a patient with a favorable response to therapy," J. Neurooncol., 64:13-20 (2003).
Okada et al., "Induction of CD8$^+$ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma", J. Clin. Oncology, 29:330-336, (2011).
Okano et al., "Identification of a novel HLA-A*0201-restricted, cytotoxic T lymphocyte epitope in a human glioma-associated antigen, interleukin 13 receptor α2 chain," Clin. Cancer Res., 8:2851-55 (2002).
Osada et al., "Dendritic cells activate antitumor immunity for malignant intracranial germ cell tumor: a case report," Jpn. J. Clin. Oncol., 31:403-406 (2001).
Parmiani et al., "Cancer immunotherapy with peptide-based vaccines: What have we achieved? Where are we going?" J. Natl. Cancer Inst., 94:805-818 (2002).
Parkhurst et al., "Identification of a shared *HLA-A\*0201*-restricted T-cell epitope from the melanoma antigen tyrosinase-related protein 2 (TRP2)," Cancer Res., 58:4895-4901 (1998).
Parney et al., "Glioma immunology and immunotherapy," Neurosurgery, 46:778-791 (2000).
Phuphanich et al., "Immune response correlation with progression-free survival in glioblastoma following dendritic cell immunotherapy (ICT-107)," J. Clin. Oncol., 28(15 suppl.):2097 (abstract) (2010).
Phuphanich et al., "Immune response correlation with progression-free surival in glioblastoma following dendritic cell immunotherapy (ICT-107)," poster presented at 2010 ASCO Annual Meeting, Jun. 4-8, 2010.
Pinilla et al., "Rapid identification of high affinity peptide ligands using positional scanning synthetic peptide combinatorial libraries," Biotechniques, 13:901-905 (1992).
Pinilla et al., "Investigation of antigen-antibody interactions using a soluble, non-support-bound synthetic decapeptide library composed of four trillion (4× 10$^{12}$) sequences," Biochem. J., 301:847-853 (1994).
Pisarra et al., "Human melanocytes and melanomas express novel mRNA isoforms of the tyrosinase-related protein-2/DOPAchrome tautomerase gene: molecular and functional characterization," J. Invest. Dermatol., 115:48-56 (2000).
Pirtskhalaishvili et al., "Cytokine-mediated protection of human dendritic cells from prostate cancer induced apoptosis is regulated by the Bcl-2 family of proteins," Br. J. Cancer, 83:506-513 (2000).
Pollack et al., "Exploitation of immune mechanisms in the treatment of central nervous system cancer," Semin. Pediatr. Neurol., 7:131-143 (2000).

Reichardt et al., "Idiotype vaccination of multiple myeloma patients using monocyte-derived dendritic cells," Haematologica, 88:1139-49 (2003).
Rissoan et al., "Reciprocal control of T helper cell and dendritic cell differentiation," Science, 283:1183-86(1999).
Rosenberg et al., "Immunologic and therapeutic evaluation of a synthetic peptide vaccine for the treatment of patients with metastatic melanoma," Nat. Med., 4:321-327 (1998).
Rudinger, J. "Characteristics of the amino acids as components of a peptide hormone sequence", Peptide Hormones, University Park Press: Baltimore, MD, pp. 107, (1976).
Salgaller et al., "Recognition of multiple epitopes in the human melanoma antigen gp100 by peripheral blood lymphocytes stimulated in vitro with synthetic peptides," Cancer Res., 55:4972-79 (1995).
Sette et al., "Epitope-based vaccines: an update on epitope identification, vaccine design and delivery", Current Opinion in Immunology, vol. 15, (2003), pp. 461-470.
Shin et al., "Antitumor effect of intratumoral administration of dendritic cell combination with vincristine chemotherapy in a murine fibrosarcoma model," Histol. Histopathol., 18:435-447 (2003).
Singh et al., "Identification of a cancer stem cell in human brain tumors," Cancer Res., 63:5821-28 (2003).
Singh, "ImmunoCellular Therapeutics, Ltd." presentation at 13th Annual BIO CEO & Investor Conference, Feb. 14, 2011, 23 pages.
Soling et al., "Dendritic cell therapy of primary brain tumors," Mol. Med., 7:659-667 (2001).
Song et al., "Strategies to improve dendritic cell-based immunotherapy against cancer," Yonsei Med. J., 45(Suppl):48-52 (2004).
Steinbrink et al., "CD4+ and CD8+ anergic T cells induced by interleukin-10-treated human dendritic cells display antigen-specific suppressor activity," Blood, 99:2468-76 (2002).
Steinman, "Some interfaces of dendritic cell biology," APMIS, 111:675-697 (2003).
Storkus et al.. "Identification of human melanoma peptides recognized by class I restricted tumor infiltrating T lymphocytes," J. Immunol., 151:3719-27 (1993).
Stupp et al., "Recent Developments in the Management of Malignant Glioma," American Society of Clinical Oncology Educational Book, 779-788 (2003).
Takagi et al., "Anti-tumor effects of dendritic and tumor cell fusions are not dependent on expression of MHC class I and II by dendritic cells," Cancer Lett., 213:49-55 (2004).
Tanaka et al., "Intraturnoral injection of dendritic cells after treatment of anticancer drugs induces tumor-specific antitumor effect in vivo," Int. J. Cancer, 101:265-269 (2002).
Tanaka et al., "Intratumoral injection of immature dendritic cells enhances antitumor effect of hyperthermia using magnetic nanoparticles," Int. J. Cancer, 116:624-633 (2005).
Tong et al., "Combined intratumoral injection of bone marrow-derived dendritic cells and systemic chemotherapy to treat pre-existing murine tumors," Cancer Res., 61:7530-35 (2001).
Tourdot et al., "A general strategy to enhance immunogenicity of low-affinity HLA-A2.1-associated peptides: implication in the identification of cryptic tumor epitopes", Eur. J. Immunol., vol. 30, (2000), pp. 3411-3421.
Voet, D. and Voet, J., "Biochemistry", Section 6-3. Chemical Evolution, John Wiley and Sons, (1990), pp. 126-128.
Wang et al., "An effective cancer vaccine modality: lentiviral modification of dendritic cells expressing multiple cancer-specific antigens," Vaccine, 24:3477-89 (2006).
Wang et al., "Identification of TRP-2 as a human tumor antigen recognized by cytotoxic T lymphocytes," J. Exp. Med., 184:2207-16 (1996).
Wei et al., "Dendritic cells expressing a combined PADRE/MUC4-derived polyepitope DNA vaccine induce multiple cytotoxic T-cell responses," Cancer Biother. Radiopharm., 23:121-128 (2008).
Weigel et al., "Dendritic cells pulsed or fused with AML cellular antigen provide comparable in vivo antitumor protective responses," Exp. Hematol., 34:1403-12 (2006).

(56) References Cited

OTHER PUBLICATIONS

Weigmann et al., "Prominin, a novel microvilli-specific polytopic membrane protein of the apical surface of epithelial cells, is targeted to plasmalemmal protrusions of non-epithelial cells", Cell Biology, Proc. Natl. Acad. Sci. USA, vol. 94, (1997), pp. 12425-12430.
Westphal et al., "Other experimental therapies for glioma," Recent Results Cancer Res., 171:155-164 (2009).
Wheeler et al., "Vaccination elicits correlated immune and clinical responses in glioblastoma multiforme patients," Cancer Res., 68:5955-64 (2008).
Wheeler et al., "Cellular immunity in the treatment of brain tumors," Clin. Neurosurg., 51:132-139 (2004).
Wheeler et al., "Clinical responsiveness of glioblastoma multiforme to chemotherapy after vaccination," Clin. Cancer Res., 10:5316-26 (2004).
Wheeler et al., "Thymic CD8+ T cell production strongly influences tumor antigen recognition and age-dependent glioma mortality," J. Immunol., 171:4927-33 (2003).
Xu et al., "Antigen-specific T-cell response from dendritic cell vaccination using cancer stem-like cell-associated antigens," Stem Cells, 27:1734-40 (2009).
Yamazaki et al., "Direct expansion of functional CD25+ CD4+ regulatory T cells by antigen-processing dendritic cells," J. Exp. Med., 198:235-247 (2003).
Yang et al., "Modulation of major histocompatibility complex Class I molecules and major histocompatibility complex-bound immunogenic peptides induced by interferon-alpha and interferon-gamma treatment of human glioblastoma multiforme," J. Neurosurg., 100:310-319 (2004).
Yang et al., "Dendritic cells infected with a vaccinia vector carrying the human gp100 gene simultaneously present multiple specificities and elicit high-affinity T cells reactive to multiple epitopes and restricted by HLA-A2 and -A3," J Immunol., 164:4204-11 (2000).
Yasuda et al., "Dendritic cell-tumor cell hybrids enhance the induction of cytotoxic T lymphocytes against murine colon cancer: a comparative analysis of antigen loading methods for the vaccination of immunotherapeutic dendritic cells," Oncol. Rep., 16:1317-24 (2006).
Young et al., "Dendritic cells stimulate primary human cytolytic lymphocyte responses in the absence of CD4+ helper T cells," J. Exp. Med., 171:1315-32 (1990).
Yu et al. "CD133 as a Potential Target of Anti-Cancer Stem Cell Immunotherapy: Identification of an HLA-A*02 Restricted CD133 Epitope. Abstract", Journal of Immunotherapy, Nov.-Dec. 2008, p. 928.
Yu et al., "Effective combination of chemotherapy and dendritic cell administration for the treatment of advanced-stage experimental breast cancer," Clin. Cancer Res., 9:285-294 (2003).
Yu et al., "Mahaley Clinical Research Award: chemosensitization of glioma through dendritic cell vaccination," Clin. Neurosurg., 53:345-351 (2006).
Yu et al., "Vaccination of malignant glioma patients with peptide-pulsed dendritic cells elicits systemic cytotoxicity and intracranial T-cell infiltration," Cancer Res., 61:842-847 (2001).
Yu et al., "Vaccination with tumor lysate-pulsed dendritic cells elicits antigen-specific, cytotoxic T-cells in patients with malignant glioma," Cancer Res., 64:4973-79 (2004).
Yuan et al., "Isolation of cancer stem cells from adult glioblastoma multiforme," Oncogene, 58:9392-9400 (2004).
Zagzag et al., "Downregulation of major histocompatibility complex antigens in invading glioma cells: stealth invasion of the brain," Lab. Invest., 85:328-341 (2005).
Zhang et al., "Antigenic profiling of glioma cells to generate allogeneic vaccines or dendritic cell-based therapeutics," Clin. Cancer Res., 13:566-575 (2007).
Zeidler et al., "Tumor cell-derived prostaglandin E2 inhibits monocyte function by interfering with CCR5 and Mac-1," FASEB J., 14:661-668 (2000).
Zhu et al., "Insertion of the dibasic motif in the flanking region of a cryptic self-determinant leads to activation of the epitope-specific T cells," J. Immunol., 175:2252-60 (2005).
Zitvogel et al., "Therapy of murine tumors with tumor peptide-pulsed dendritic cells: dependence on T cells, B7 costimulation, and T helper cell-1 associated cytokines," J. Exp. Med., 183:87-97 (1996).
International Search Report of International Application No. PCT/US07/79846, mailed Jul. 14, 2008, 10 pages.
International Search Report of International Application No. PCT/US07/79857, mailed Apr. 8, 2008, 9 pages.
International Preliminary Report on Patentability for App. Ser. No. PCT/US07/079846, mailed Apr. 9, 2009, 5 pages.
International Preliminary Report on Patentability for App. Ser. No. PCT/US07/079857, mailed Apr. 9, 2009, 5 pages.
Supplementary European Search Report for European Application No. 09812172.6, mailed May 4, 2012, 6 pages.
USPTO Final Office Action in U.S. Appl. No. 11/864,177, mailed May 13, 2011, 18 pages.
USPTO Non-Final Office Action in U.S. Appl. No. 11/864,177, mailed Aug. 26, 2010, 16 pages.
USPTO Final Office Action in U.S. Appl. No. 11/863,990, mailed May 12, 2011, 18 pages.
USPTO Non-Final Office Action in U.S. Appl. No. 11/863,990, mailed Aug. 26, 2010, 15 pages.
Feng et al, "P55, an Immunogenic but Nonprotective 55-Kilodalton Borrelia burgdorferi Protein in Murine Lyme Disease", Infection and Immunity, pp. 363-365 (1996).
Examination Report issued in corresponding Canadian Application No. 2,700,436 on Dec. 2, 2015, Examiner Nicole Harris, 3 pages.
Office Action (Non-Final) issued in related U.S. Appl. No. 11/863,990 on Feb. 6, 2014, Examiner Lei Yao, 12 pages.
Office Action (Final) issued in related U.S. Appl. No. 11/862,135 on Jan. 6, 2010, Examiner Joanne Hama, 12 pages.
Office Action (Non-Final) issued in related U.S. Appl. No. 11/862,135 on Jul. 23, 2010, Examiner Jul. 23, 2010, 10 pages.
Office Action (Non-Final) issued in related U.S. Appl. No. 13/365,666 on May 22, 2014, Examiner Amy E. Juedes, 18 pages.
Office Action (Non-Final) issued in related U.S. Appl. No. 12/552,945 on Jun. 5, 2014, Examiner Maria Gomez Leavitt, 31 pages.
Office Action (Non-Final) issued in related U.S. Appl. No. 13/826,737 on Jun. 13, 2014, Examiner Maria Gomez Leavitt, 37 pages.
Office Action (Final) issued in related U.S. Appl. No. 13/826,737 on Oct. 24, 2014, Examiner Maria Gomez Leavitt, 38 pages.
Office Action (Non-Final) issued in related U.S. Appl. 13/826,737 on May 11, 2015, Examiner Maria Gomez Leavitt, 25 pages.
International Preliminary Report on Patenability; PCT/US2014/016562; Aug. 27, 2015; 10 pp.
International Preliminary Report on Patentability, PCT/US2014/16610; Aug. 27, 2015; 11 pp.
Xu et al.; "Isolation of tumour stem-like cells from benign tumours"; *British Journal of Cancer*; (2009) 101, pp. 303-311.

* cited by examiner

* Indicate p<0.05 compared with CTL gp100 (2M)

PBMC from Pt. 1

PBMC from Pt. 2

* Indicates p<0.05 compared with CTL Her-2 native peptide (No.52)

CANCER VACCINES AND VACCINATION METHODS

CROSS-REFERENCE TO RELATED APPLICATIONS

This application is a divisional of U.S. patent application Ser. No. 11/864,177, filed on Sep. 28, 2007, now U.S. Pat. No. 8,097,256, which claims the benefit of priority from U.S. Provisional Patent Application Ser. No. 60/827,260, filed on Sep. 28, 2006. The entire contents of the foregoing applications are incorporated herein by reference.

TECHNICAL FIELD

The invention relates to methods and compositions for the treatment of cancers, such as neural cancers.

BACKGROUND

Brainstem gliomas are a heterogeneous group of tumors that can be distinguished by age of onset, clinical and radiological presentation, and biological behavior. The diagnosis of a diffuse brainstem glioma is based upon typical imaging, dispensing with the need for surgery in the majority of cases. Radiation therapy is the mainstay of treatment for children with diffuse brainstem gliomas. The role of chemotherapy for these children is not clear, and it is, in general, employed in the context of an investigational study. Less than 10% of children with diffuse brainstem gliomas survive 2 years. In contrast to childhood brainstem gliomas, adult brainstem gliomas are rare and poorly understood. Mean age at onset is 34 years. The main presenting symptoms are gait disturbance (61%), headache (44%), weakness of the limbs (42%) and diplopia (40%). The diagnosis of a brainstem glioma is uniformly lethal. Glioblastoma is the most common and most malignant primary brain tumor. Survival with surgery, radiation, and chemotherapy ranges from 12 to 15 months.

The potential therapy is immunotherapy, which is a form of cancer treatment that activates the immune system to attack and eradicate cancer cells. Cytotoxic T lymphocytes ("CTL") are critical to a successful antitumor immune response. T cells that attack cancer cells require the presentation of tumor antigens to naïve T cells that undergo activation, clonal expansion, and ultimately exert their cytolytic effector function. Unfortunately, this mechanism is defective in patients with malignant gliomas. Effective antigen presentation is essential to successful CTL effector function. Thus, the development of a successful strategy to initiate presentation of tumor antigens to T cells can be important to an immunotherapeutic strategy for malignant brain tumors (Liu et al., Expert Rev. Vaccines, 5(2):233-247, 2006).

Various immunotherapies have been investigated for malignant glioma, including antibody- and cytokine-based therapies, cancer vaccines, and adoptive cellular therapies. However, such treatments for central nervous system gliomas have not been discovered as quickly as therapies for more immunogenic tumors, e.g., melanoma. This is partly due to the relative lack of defined glioma-associated antigens that can be targeted by the immune system. In recent years, several tumor-associated antigens ("TAA") have been identified and characterized for different cancers, including breast, colon, renal, and melanoma.

Some tumor-associated antigens have been identified for human glioma cells, including tyrosinase-related protein (TRP)-2 (a melanoma differentiation antigen), Melanoma-associated Antigen-1 (MAGE-1), a cancer/testis antigen, HER-2/neu (selectively overexpressed in tumors), interleukin-13 (IL-13) receptor α2, gp100 (a melanoma differentiation antigen), and Antigen isolated from Immunoselected Melanoma-2 (AIM-2), a novel tumor antigen (Liu et al., Oncogene, 24(33): 5226-5234, 2005; Liu et al., J. Immunother., 26(4): 301-312, 2003; Liu et al., J. Immunother., 27(3): 220-226, 2004; Liu et al., Canc. Res., 64: 4980-4986, 2004).

With respect to these specific antigens, a vaccine consisting of dendritic cells pulsed with MAGE-1 peptide has been used in melanoma patients to induce clinical and systemic tumor-specific responses without provoking major side effects. It has also been shown that melanoma patients immunized with a melanoma cell vaccine induce antibody responses to recombinant MAGE-1 antigen. In addition, several clinical trials have indicated that gp100 is a highly immunogenic antigen in melanoma patients, and showed a strong correlation between T cell recognition of the gp100 antigen and clinical responses. The HER-2 oncogenic protein has been well-defined in the art, and a HER-2 specific vaccine has been tested in human clinical trials. Early results showed the immunity elicited by the vaccine was durable even after vaccinations ended.

The immunogenicity and regulation of HER-2, gp100, and MAGE-1 in glioblastoma multiforme ("GBM") have been investigated. Liu et al. (Canc. Res., 64: 4980-4986, 2004) describes that the majority of GBMs express these antigens and process the dominant epitopes. It was also determined that CTLs recognize these antigens on GBMs, and that recognition is determined by both antigen expression and MHC expression on the cell surfaces. These results showed that tumor antigen expression in GBM cells correlates with tumor cell recognition by CTLs.

With respect to the antigen AIM-2, it has been shown that both non-spliced and spliced AIM-2 transcripts are expressed in many tumor types. One particular melanoma-reactive T cell clone recognizes a peptide from non-spliced AIM-2, but not from spliced AIM-2. GBMs express AIM-2—spliced and non-spliced forms—and process the dominant epitope from non-spliced AIM-2, allowing CTL recognition of peptides. In addition, AIM-2 CTL have been generated in certain patients by vaccination with dendritic cells pulsed with tumor lysates, and that the ability of CTLs to recognize autologous tumor cells was increased by these vaccinations.

TRP-2 is a naturally processed, immunogenic tumor antigen in mice and humans. Vaccination with dendritic cells pulsed with TRP-2 has been shown to generate TRP-2-specific CTLs and immunity against B16 melanoma tumors, delay B16 tumor growth, and prolong mouse survival. It was also demonstrated that immunization with the human TRP-2 gene elicited autoantibodies and autoreactive cytotoxic T cells. TRP-2-specific cytotoxic T cell activity has been detected in patients after vaccination with dendritic cells pulsed with autologous tumor lysate. In a dendritic cell-based phase I clinical trial, TRP-2 peptide-specific CTLs were induced in patients without observed side effects or autoimmune reactions. It has also been demonstrated that GBM cells from postvaccination resections show lower TRP-2 expression and higher sensitivity to chemotherapeutic drugs than autologous cell lines from pre-vaccination resections.

With the diagnosis of a brainstem glioma being uniformly lethal, glioblastoma as the most common and most malignant primary brain tumor, and survival with surgery, radiation, and chemotherapy only ranging from 12 to 15 months, there exists a significant need in the art for the development of novel therapeutic measures.

SUMMARY

The invention is based, in part, on the discovery that immunizing glioma patients with antigen presenting cells (APC) loaded with unique combinations of multiple tumor antigens induces therapeutic immune responses that can be used to treat these patients to provide significantly increased survival. Accordingly, methods for inducing immune responses in cancer patients (e.g., neural cancer patients, such as glioma patients) against tumor antigens are provided herein. The methods use as vaccines APC, such as dendritic cells (DC), that present specific combinations of multiple different tumor antigens. Also provided are compositions that include the cells and the antigens.

Various embodiments provide for vaccines including epitopes of any combination of four or more of the following antigens: tyrosinase-related protein (TRP)-2, Melanoma-associated Antigen-1 (MAGE-1), HER-2, IL-13 receptor α2, gp100, and AIM-2. For example, the vaccines include epitopes (e.g., peptide fragments) of any four of the antigens, any five of the antigens, or all six of the antigens. In some embodiments, the vaccines include epitopes for additional tumor antigens.

Additional embodiments of the present invention provide for vaccines loaded with one or more superagonist epitopes for some or all of the following antigens: TRP-2, MAGE-1, HER-2, IL-13 receptor α2, gp100, and AIM-2. A "superagonist" or "superantigen" peptide is a peptide that includes one or more mutations (e.g., one, two, or three amino acid changes, relative to a native sequence) and that elicits an antigen-specific immunological response that is more potent than a response elicited by a peptide having a native sequence. For example, a superagonist peptide stimulates higher levels of IFN-γ release by antigen-specific T cells, as compared to T cells stimulated with the native peptide. The increase in levels of IFN-γ release stimulated by a superagonist peptide are higher than levels stimulated by a native peptide by a statistically significant amount. In some embodiments, a superagonist stimulates IFN-γ levels that are at least 5%, 10%, 25%, 50%, 100%, 200%, or 500% higher than elicited by the native peptide.

The vaccines of the present invention can be used to treat a cancer, e.g., a neural cancer. In particular embodiments, the vaccines can be used to treat gliomas. In other embodiments the vaccines can be used to treat glioblastoma multiforme (GBM). In other embodiments, the vaccines can be used to treat astrocytomas. In various embodiments, the vaccines are administered in an amount sufficient to induce an immune response against the antigens (e.g., a T cell response).

The vaccines can include autologous dendritic cells. In alternative embodiments, the vaccines can include allogeneic dendritic cells. Dendritic cells suitable for use in the vaccination methods disclosed herein can be isolated or obtained from any tissue in which such cells are found, or can be otherwise cultured and provided. Dendritic cells can be found in, for example, but in no way limited to, the bone marrow, peripheral blood mononuclear cells (PBMCs) of a mammal, or the spleen of a mammal. Additionally, any suitable media that promote the growth of dendritic cells can be used in accordance with the present invention, and can be readily ascertained by one skilled in the art.

The dendritic cells in the vaccines described herein can be pulsed with any or all of the following antigens (i.e., incubated for a sufficient time to allow uptake and presentation of peptides of the antigens on MHC molecules): TRP-2, MAGE-1, HER-2, IL-13 receptor α2, gp100, and AIM-2, or epitopes of these antigens (e.g., peptide epitopes 7-25 amino acids in length). The epitopes are, for example, peptides 7 to 13 (e.g., 8 to 10, e.g., 9) amino acids in length.

The dendritic cells present epitopes corresponding to the antigens at a higher average density than epitopes present on dendritic cells exposed to a tumor lysate (e.g., a neural tumor lysate) (e.g., at a density that is at least 5%, 10%, 25%, 50%, 100%, or 200% higher). The dendritic cells can acquire the antigens or portions thereof (e.g., peptide epitopes) by incubation with the antigens in vitro (e.g., wherein cells acquire antigens by incubation with the combination of the antigens simultaneously, or with a subset of antigens, e.g., in separate pools of cells). In some embodiments, the dendritic cells are incubated with a composition including the peptides, wherein the peptides are synthetic peptides and/or were isolated or purified prior to incubation with the cells. In some embodiments, dendritic cells are engineered to express the peptides by recombinant means (e.g., by introduction of a nucleic acid that encodes the full length antigen or a portion thereof, e.g., the peptide epitope).

In some embodiments, the synthetic peptides include a synthetic peptide having a dibasic motif (i.e., Arg-Arg, Lys-Lys, Arg-Lys, or Lys-Arg) at the N-terminus and a dibasic motif at the C-terminus. In some embodiments, the synthetic peptides include a HER2 peptide including one of the following amino acid sequences: RRILHNGAYSLRR (SEQ ID NO:1) or RRKIFGSLAFLRR (SEQ ID NO:2).

The dendritic cells can include a peptide including an amino acid sequence corresponding to an epitope of TRP-2, MAGE-1, HER-2, IL-13 receptor α2, gp100, and AIM-2, described herein. For example, the dendritic cells include at least one of the following sequences: RSDSGQQARY (SEQ ID NO:3) from AIM-2; EADPTGHSY (SEQ ID NO:4) from MAGE-1; SVYDFFVWL (SEQ ID NO:5) from TRP-2; ITDQVPFSV (SEQ ID NO:6) from gp100; KIFGSLAFL (SEQ ID NO:7) from HER-2; and WLPFGFILI (SEQ ID NO:8) from IL-13 receptor α2. In some embodiments, the peptide is amidated at the C-terminus.

In alternative embodiments, the dendritic cells in the vaccines are pulsed with any or all of superagonist epitopes of some or all of the aforementioned antigens. The superagonist antigens have certain amino acid substitutions that generate a more potent immune response than the natural epitopes. In some embodiments, the dendritic cells are pulsed with a peptide epitope including one or both of the following superagonist peptide sequences: YMDQVPYSV (SEQ ID NO:65) from gp100; or FMANVAIPHL (SEQ ID NO:68) from HER-2. In some embodiments, the dendritic cells are pulsed with a peptide epitope including one of the following peptide sequences: FLDQVPYSV (SEQ ID NO:63) from gp100; ILDQVPFSV (SEQ ID NO:66) from gp100; IMDQVPFSV (SEQ ID NO:67) from gp100, FMHNVPIPYL (SEQ ID NO:69) from HER-2; or FYANVPSPHL (SEQ ID NO:70) from HER-2. In some embodiments, the peptide is amidated at the C-terminus. Superagonist peptides can be used in combination with any of the peptides described herein.

In some embodiments, the dendritic cells include more than one peptide epitope for a given antigen, e.g., wherein the dendritic cells comprise two, three, four, or more peptide epitopes from AIM-2, and/or two, three, four, or more peptide epitopes from MAGE-1, and so forth.

Other embodiments of the present invention provide for methods of treating cancers (e.g., neural cancers, e.g., gliomas) using the inventive vaccines. In one embodiment, the method of treating gliomas comprises administering a vaccine as described herein to a patient. Other embodiments provide for methods of treating cancers such as carcinomas, or brain metastatic cancers.

The vaccines can be administered one or more times to a patient to impart beneficial results. The vaccines can be administered prior or post surgical resection of the tumor. One skilled in the art will be able to determine the appropriate timing for administering the vaccine. The timing of the first and/or subsequent dose(s) of the vaccine can depend on a variety of factors, including, but not limited to a patient's health, stability, age, and weight. The vaccine can be administered at any appropriate time interval; for example, including but not limited to, once per week, once every two weeks, once every three weeks, once per month. In one embodiment, the vaccine can be administered indefinitely. In one embodiment, the vaccine can be administered three times in two week intervals. Appropriate dosages of the vaccines also depends on a variety of factors, including, but not limited to, a patient's health, stability, age, and weight. In one embodiment, the vaccine includes from about $10^5$ to about $10^9$ tumor antigen-pulsed dendritic cells. In another embodiment, the vaccine includes about $10^7$ tumor antigen-pulsed dendritic cells.

In some embodiments, the methods of treating cancers include identifying a patient whose tumor expresses one or more of TRP-2, MAGE-1, HER-2, IL-13 receptor α2, gp100, and AIM-2, prior to the treatment. For example, a method can include evaluating whether a tumor in a glioma patient expresses HER-2, and, if the tumor expresses HER-2, administering the vaccine to the patient. Patients whose tumors are positive for other tumor antigens can also be identified and selected for treatment.

The vaccines can be administered in conjunction with other therapeutic treatments; for example, chemotherapy and/or radiation. In some embodiments, the inventive vaccines are administered by injection (i.e., intravenous, intraarterial, etc.). In other embodiments, the inventive vaccines are administered directly into or in close proximity of the tumor. In other embodiments, the inventive vaccines are administered directly into or in close proximity of the site of the resected tumor.

In other embodiments, methods of producing the inventive vaccines are provided. In some embodiments, the vaccines are made by obtaining dendritic cells from a subject and loading the dendritic cells with the antigens. The dendritic cells can be autologous or allogeneic.

In some embodiments, a method of producing the vaccine includes obtaining bone marrow derived mononuclear cells from a subject, culturing the mononuclear cells in vitro under conditions in which mononuclear cells become adherent to a culture vessel, selecting a subset of the mononuclear cells including adherent cells, culturing the subset of cells in the presence of one or more cytokines (e.g., GM-CSF, IL-4, TNF-α) under conditions in which the cells differentiate into antigen presenting cells, culturing the adherent cells in the presence of synthetic peptides, the peptides including amino acid sequences corresponding to epitopes of at least four of the following six antigens: TRP-2, MAGE-1, HER-2, IL-13 receptor α2, gp100, and AIM2, under conditions in which the cells present the peptides on major histocompatibility class I molecules, thereby preparing a cell vaccine. In some embodiments, the bone marrow derived cells are obtained from a patient with a cancer (e.g., a neural cancer, e.g., glioma), and the cell vaccine is prepared to treat the patient.

In some embodiments, the synthetic peptides include a synthetic peptide having a dibasic motif (i.e., Arg-Arg, Lys-Lys, Arg-Lys, or Lys-Arg) at the N-terminus and a dibasic motif at the C-terminus. In some embodiments, the synthetic peptides include a HER2 peptide including one of the following amino acid sequences: RRILHNGAYSLRR (SEQ ID NO:1) or RRKIFGSLAFLRR (SEQ ID NO:2).

In another aspect, the invention features a peptide fragments of TRP-2, MAGE-1, IL-13 receptor α2, gp100, and AIM2, modified to include dibasic motifs at the N-terminus and C-terminus (e.g., a peptide having one of the following amino acid sequences: RRRSDSGQQARYRR (SEQ ID NO:9); RREADPTGHSYRR (SEQ ID NO:10); RRSVYDFFVWLRR (SEQ ID NO:11); RRITDQVPFSVRR (SEQ ID NO:12); and RRWLPFGFILIRR (SEQ ID NO:13). Combinations of the peptides, and compositions including the peptides are also provided.

This invention also provides immunogenic compositions that include, or encode the combinations of antigens described herein, and methods of using the compositions. For example, preparations of HER-2, AIM-2, MAGE-1, TRP-2, IL-13 receptor α2, and gp100 peptides, for use as cancer vaccines (e.g., peptide vaccines, or nucleic acids encoding the peptides) are provided. The invention also provides immunogenic compositions that include a superagonist peptide, e.g., a superagonist peptide epitope corresponding to one or more of HER-2, AIM-2, MAGE-1, TRP-2, IL-13 receptor α2, and gp100.

"Beneficial results" can include, but are in no way limited to, lessening or alleviating the severity of the disease condition, preventing the disease condition from worsening, curing the disease condition, and prolonging a patient's life or life expectancy.

"Cancer" and "cancerous" refer to or describe the physiological condition in mammals that is typically characterized by unregulated cell growth. Examples of neural cancers include cancers of the brain and spinal cord such as gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, neuroblastomas, and craniopharyngiomas. GBM, glioblastomas, astrocytomas, ependymomas, and oligodendrogliomas are types of gliomas.

"Conditions" and "disease conditions," as used herein can include, but are in no way limited to any form of neoplastic cell growth and proliferation, whether malignant or benign, pre-cancerous and cancerous cells and tissues; in particular, gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, neuroblastomas, and craniopharyngiomas.

"Mammal" as used herein refers to any member of the class Mammalia, including, without limitation, humans and nonhuman primates such as chimpanzees and other apes and monkey species; farm animals such as cattle, sheep, pigs, goats, and horses; domestic mammals such as dogs and cats; laboratory animals including rodents such as mice, rats, and guinea pigs, and the like. The term does not denote a particular age or sex. Thus, adult and newborn subjects, as well as fetuses, whether male or female, are intended to be included within the scope of this term. The terms "patient" and "subject" are used interchangeably herein, and cover mammals including humans.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Treatment" and "treating," as used herein refer to both therapeutic treatment and prophylactic or preventative measures, wherein the object is to inhibit or slow down (lessen) the targeted disorder (e.g., cancer, e.g., glioma) or symptom of the disorder, or to improve a symptom, even if the treatment is partial or ultimately unsuccessful. Those in need of treatment include those already diagnosed with the disorder as well as those prone or predisposed to contract the disorder or those in whom the disorder is to be prevented. For example, in tumor (e.g., cancer) treatment, a therapeutic agent can directly decrease the pathology of tumor cells, or render the tumor cells more susceptible to treatment by other therapeutic agents or by the subject's own immune system.

"Tumor," as used herein refers to all neoplastic cell growth and proliferation, whether malignant or benign, and all pre-cancerous and cancerous cells and tissues.

A "dendritic cell" or "DC" is an antigen presenting cell (APC) that typically expresses high levels of MHC molecules and co-stimulatory molecules, and lacks expression of (or has low expression of) markers specific for granulocytes, NK cells, B lymphocytes, and T lymphocytes, but can vary depending on the source of the dendritic cell. DCs are able to initiate antigen specific primary T lymphocyte responses in vitro and in vivo, and direct a strong mixed leukocyte reaction (MLR) compared to peripheral blood leukocytes, splenocytes, B cells and monocytes. Generally, DCs ingest antigen by phagocytosis or pinocytosis, degrade it, present fragments of the antigen at their surface and secrete cytokines.

Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); Sambrook and Russel, Molecular Cloning: A Laboratory Manual 3rd ed., Cold Spring Harbor Laboratory Press (Cold Spring Harbor, N.Y. 2001); and Lutz et al., Handbook of Dendritic Cells: Biology, Diseases and Therapies, J. Wiley & Sons (New York, N.Y. 2006), provide one skilled in the art with a general guide to many of the terms used in the present application. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, the drawings, and from the claims.

DETAILED DESCRIPTION

Figure 1:
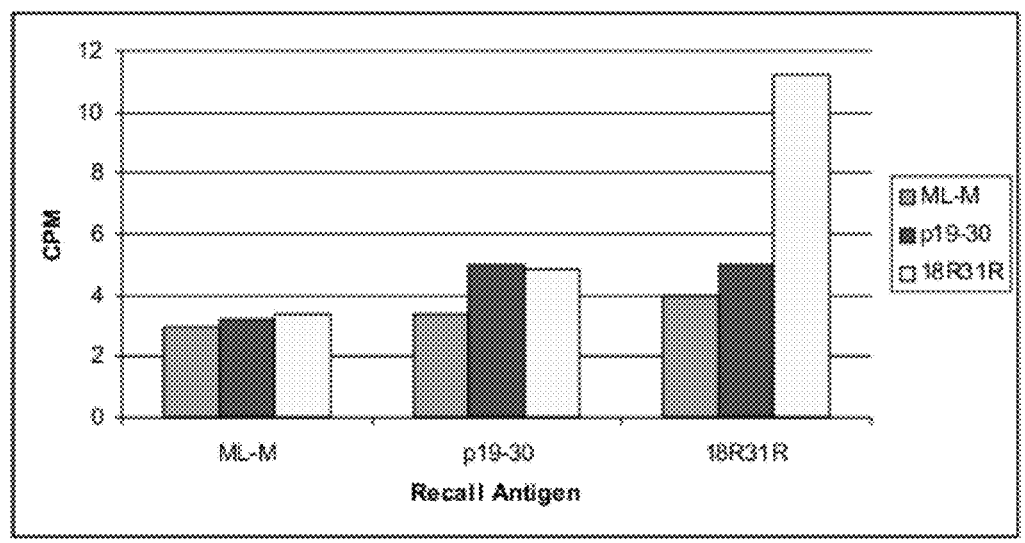
FIG. 1 is a graph depicting levels of epitope-specific T cell responses in mice following immunization IV with mouse lysozyme-M (ML-M), a mouse lysozyme peptide (p19-30), and a mouse lysozyme peptide modified with dibasic residues (18R31R), as measured by cell proliferation in vitro. T cells were isolated from lymph nodes of the animals (3 animals per group) and response to each immunogen was measured.

The invention provides, inter alia, methods and compositions for treating gliomas by administering cells presenting unique combinations of tumor antigens. Vaccination with dendritic cells or GM-CSF secreting cells is safe and elicits a cytotoxic T cell response associated with memory T cells with dendritic cells and naïve T cells with GM-CSF (Yu, J. S., Wheeler, C. J., Zeltzer, P. M., et al., Cancer Res, 61: 842-847, 2001). The combinations of antigens described herein elicit therapeutic, tumor-specific immune responses. The combinations of antigens described herein stimulate a more heterogeneous immune response than would be elicited with a single antigen, and thus are particularly beneficial for targeting tumors. For example, a tumor may evolve such that expression of a given tumor antigen is turned off. Thus, an immune response against multiple tumor antigens is more likely to provide effective therapy in this context, and can provide significant therapeutic benefits for various patient populations. The present compositions and methods feature combinations including epitopes from four, five, or six of the following: TRP-2, MAGE-1, HER-2, IL-13 receptor α2, gp100, and AIM-2. Tables 1 and 2 lists amino acid sequences of these antigens and peptide epitopes of the antigens.

Tumor Antigens

AIM-2

AIM-2 is expressed in a variety of tumor types, including neuroectodermal tumors, and breast, ovarian and colon carcinomas. Table 1 provides an amino acid sequence of human AIM-2 (also available in GenBank under accession no. AAD51813.1, GI: 5802881).

The following is an exemplary sequence of an AIM-2 HLA epitope: RSDSGQQARY (SEQ ID NO:3) (also shown in Table 2, below). This epitope is encoded by an alternative open reading frame (see Harada et al., J. Immunother., 24(4):323-333, 2001).

GP100

Gp100 is a glycoprotein preferentially expressed in melanocytes. Table 1 provides an amino acid sequence of human gp100 (also available in GenBank under accession no. NP_008859.1, GI: 5902084). Table 2 lists exemplary HLA epitopes from gp100.

HER-2

HER-2 (also known as HER-2/neu, and c-erbB2) is a transmembrane glycoprotein with tyrosine kinase activity. HER-2 is overexpressed in a variety of tumor types.

Table 1 provides an amino acid sequence of human HER-2 (also available in GenBank under accession no. NP_004439.2, GI: 54792096). Table 2 lists exemplary HLA epitopes from HER-2.

IL-13 Receptor α2

IL-13 receptor α2 is a non-signaling component of the multimeric IL-13 receptor. An exemplary human IL-13 receptor α2 amino acid sequence is shown in Table 1 (also available in Genbank under acc. no. NP_000631.1, GI: 10834992).

The following is an exemplary sequence of an IL-13 receptor α2 HLA epitope, corresponding to amino acids 345-354 of the above sequence: WLPFGFILI (SEQ ID NO:8) (also shown in Table 2).

MAGE-1

MAGE-1 is a cancer/testis antigen originally identified in melanoma. Table 1 provides an amino acid sequence of human MAGE-1 (also available in GenBank under accession no. NP_004979.3, GI: 148276977). Table 2 lists exemplary MAGE-1 HLA peptide epitopes.

TRP-2

TRP-2 is a dopachrome tautomerase involved in melanogenesis (Aroca et al., Biochim Biophys Acta., 1035(3):266-75, 1990). Human TRP-2 shares 84% identity with murine TRP-2 (Yokoyama et al., Biochim. Biophys. Acta., 1217: 317-321, 1994). TRP-2 has five isoforms generated by alternative poly(A) site usage or alternative splicing, including the isoforms designated as TRP-2-6b, TRP-2-INT2, TRP-2-LT, and TRP-2-8b. See Liu et al., J. Immunother., 26(4):301-312, 2003; Pisarra et al., J. Invest. Dermatol., 115:48-56, 2000; Khong and Rosenberg, J. Immunol., 168: 951-956, 2002; and Lupetti et al., J. Exp. Med., 188:1005-1016, 1998. Epitopes of each of these isoforms are useful for the vaccines and methods disclosed herein.

Table 1 provides a sequence of human TRP-2 which has 519 amino acids (also available in GenBank under accession no. NP_001913.2, GI:6041667). The amino acid sequence of another human TRP-2 isoform that has 552 amino acids is available in Genbank under acc. no. ABI73976.1, GI:114384149. Table 2 lists exemplary TRP-2 HLA epitopes.

TABLE 1

| Tumor antigen | Amino acid sequence |
|---|---|
| AIM-2 | MVVLGMQTEEGHCIMLRGLAPSLGGTQVICKVVGLPSSIGFNTSSHLLFPATLQGAPTHFPCRWRQGGST DNPPA (SEQ ID NO: 14) |
| gp100 | MDLVLKRCLLHLAVIGALLAVGATKVPRNQDWLGVSRQLRTKAWNRQLYPEWTEAQRLDCWRGGQVSLKV SNDGPTLIGANASFSIALNFPGSQKVLPDGQVIWVNNTIINGSQVWGGQPVYPQETDDACIFPDGGPCPS GSWSQKRSFVYVWKTWGQYWQVLGGPVSGLSIGTGRAMLGTHTMEVTVYHRRGSRSYVPLAHSSSAFTIT DQVPFSVSVSQLRALDGGNKHFLRNQPLTFALQLHDPSGYLAEADLSYTWDFGDSSGTLISRALVVTHTY LEPGPVTAQVVLQAAIPLTSCGSSPVPGTTDGHRPTAEAPNTTAGQVPTTEVVGTTPGQAPTAEPSGTTS VQVPTTEVISTAPVQMPTAESTGMTPEKVPVSEVMGTTLAEMSTPEATGMTPAEVSIVVLSGTTAAQVTT TEWVETTARELPIPEPEGPDASSIMSTESITGSLGPLLDGTATLRLVKRQVPLDCVLYRYGSFSVTLDIV QGIESAEILQAVPSGEGDAFELTVSCQGGLPKEACMEISSPGCQPPAQRLCQPVLPSPACQLVLHQILKG GSGTYCLNVSLADTNSLAVVSTQLIMPGQEAGLGQVPLIVGILLVLMAVVLASLIYRRRLMKQDFSVPQL PHSSSHWLRLPRIFCSCPIGENSPLLSGQQV (SEQ ID NO: 15) |
| HER-2 | MELAALCRWGLLLALLPPGAASTQVCTGTDMKLRLPASPETHLDMLRHLYQGCQVVQGNLELTYLPTNAS LSFLQDIQEVQGYVLIAHNQVRQVPLQRLRIVRGTQLFEDNYALAVLDNGDPLNNTTPVTGASPGGLREL QLRSLTEILKGGVLIQRNPQLCYQDTILWKDIFHKNNQLALTLIDTNRSRACHPCSPMCKGSRCWGESSE DCQSLTRTVCAGGCARCKGPLPTDCCHEQCAAGCTGPKHSDCLACLHFNHSGICELHCPALVTYNTDTFE SMPNPEGRYTFGASCVTACPYNYLSTDVGSCTLVCPLHNQEVTAEDGTQRCEKCSKPCARVCYGLGMEHL REVRAVTSANIQEFAGCKKIFGSLAFLPESFDGDPASNTAPLQPEQLQVFETLEEITGYLYISAWPDSLP DLSVFQNLQVIRGRILHNGAYSLTLQGLGISWLGLRSLRELGSGLALIHHNTHLCFVHTVPWDQLFRNPH QALLHTANRPEDECVGEGLACHQLCARGHCWGPGPTQCVNCSQFLRGQECVEECRVLQGLPREYVNARHC LPCHPECQPQNGSVTCFGPEADQCVACAHYKDPPFCVARCPSGVKPDLSYMPIWKFPDEEGACQPCPINC THSCVDLDDKGCPAEQRASPLTSIISAVVGILLVVVLGVVFGILIKRRQQKIRKYTMRRLLQETELVEPL TPSGAMPNQAQMRILKETELRKVKVLGSGAFGTVYKGIWIPDGENVKIPVAIKVLRENTSPKANKEILDE AYVMAGVGSPYVSRLLGICLTSTVQLVTQLMPYGCLLDHVRENRGRLGSQDLLNWCMQIAKGMSYLEDVR LVHRDLAARNVLVKSPNHVKITDFGLARLLDIDETEYHADGGKVPIKWMALESILRRRFTHQSDVWSYGV TVWELMTFGAKPYDGIPAREIPDLLEKGERLPQPPICTIDVYMIMVKCWMIDSECRPRFRELVSEFSRMA RDPQRFVVIQNEDLGPASPLDSTFYRSLLEDDDMGDLVDAEEYLVPQQGFFCPDPAPGAGGMVHHRHRSS STRSGGGDLTLGLEPSEEEAPRSPLAPSEGAGSDVFDGDLGMGAAKGLQSLPTHDPSPLQRYSEDPTVPL PSETDGYVAPLTCSPQPEYVNQPDVRPQPPSPREGPLPAARPAGATLERPKTLSPGKNGVVKDVFAFGGA VENPEYLTPQGGAAPQPHPPPAFSPAFDNLYYWDQDPPERGAPPSTFKGTPTAENPEYLGLDVPV (SEQ |

TABLE 1-continued

| Tumor antigen | Amino acid sequence |
|---|---|
| | ID NO: 16) |
| IL-13 receptor α2 | MAFVCLAIGCLYTFLISTTFGCTSSSDTEIKVNPPQDFEIVDPGYLGYLYLQWQPPLSLDHFKECTVEYE LKYRNIGSETWKTIITKNLHYKDGFDLNKGIEAKIHTLLPWQCTNGSEVQSSWAETTYWISPQGIPETKV QDMDCVYYNWQYLLCSWKPGIGVLLDTNYNLFYWYEGLDHALQCVYDYIKADGQNIGCRFPYLEASDYKDF YICVNGSSENKPIRSSYFTFQLQNIVKPLPPVYLTFTRESSCEIKLKWSIPLGPIPARCFDYEIEIREDD TTLVTATVENETYTLKTTNETRQLCFVVRSKVNIYCSDDGIWSEWSDKQCWEGEDLSKKTLLRFWLPFGF ILILVIFVTGLLLRKPNTYPKMIPEFFCDT (SEQ ID NO: 17) |
| MAGE-1 | MSLEQRSLHCKPEEALEAQQEALGLVCVQAATSSSSPLVLGTLEEVPTAGSTDPPQSPQGASAFPTTINF TRQRQPSEGSSSREEEGPSTSCILESLFRAVITKKVADLVGFLLLLKYRAREPVTKAEMLESVIKNYKHCF PEIFGKASESLQLVFGIDVKEADPTGHSYVLVTCLGLSYDGLLGDNQIMPKTGFLIIVLVMIAMEGGHAP EEEIWEELSVMEVYDGREHSAYGEPRKLLTQDLVQEKYLEYRQVPDSDPARYEFLWGPRALAETSYVKVL EYVIKVSARVRFFFPSLREAALREEEEGV (SEQ ID NO: 18) |
| TRP-2 | MSPLWWGFLLSCLGCKILPGAQGQFPRVCMTVDSLVNKECCPRLGAESANVCGSQQGRGQCTEVRADTRP WSGPYILRNQDDRELWPRKFFHRTCKCTGNFAGYNCGDCKFGWTGPNCERKKPPVIRQNIHSLSPQEREQ FLGALDLAKKRVHPDYVITTQHWLGLLGPNGTQPQFANCSVYDFFVWLHYYSVRDTLLGPGRPYRAIDFS HQGPAFVTWHRYHLLCLERDLQRLIGNESFALPYWNFATGRNECDVCTDQLFGAARPDDPTLISRNSRFS SWETVCDSLDDYNHLVTLCNGTYEGLLRRNQMGRNSMKLPTLKDIRDCLSLQKFDNPPFFQNSTFSFRNA LEGFDKADGTLDSQVMSLHNLVHSFLNGTNALPHSAANDPIFVVLHSFTDAIFDEWMKRFNPPADAWPQE LAPIGHNRMYNMVPFFPPVTNEELFLTSDQLGYSYAIDLPVSVEETPGWPTTLLVVMGTLVALVGLFVLL AFLQYRRLRKGYTPLMETHLSSKRYTEEA (SEQ ID NO : 19) |

TABLE 2

Tumor Antigen Peptides

| Tumor antigen | Position in sequence | Peptide sequence |
|---|---|---|
| AIM-2 | | RSDSGQQARY (SEQ ID NO: 3) |
| gp100 | 71-78 | SNDGPTLI (SEQ ID NO: 20) |
| gp100 | 154-162 | KTWGQYWQV (SEQ ID NO: 21) |
| gp100 | 209-217 | ITDQVPFSV (SEQ ID NO: 6) |
| gp100 | 280-288 | YLEPGPVTA (SEQ ID NO: 22) |
| gp100 | 613-622 | SLIYRRRLMK (SEQ ID NO: 23) |
| gp100 | 614-622 | LIYRRRLMK (SEQ ID NO: 24) |
| gp100 | 619-627 | RLMKQDFSV (SEQ ID NO: 25) |
| gp100 | 639-647 | RLPRIFCSC (SEQ ID NO: 26) |
| gp100 | 476-485 | VLYRYGSFSV (SEQ ID NO: 27) |
| HER-2 | 5-13 | ALCRWGLLL (SEQ ID NO: 28) |
| HER-2 | 8-16 | RWGLLLALL (SEQ ID NO: 29) |
| HER-2 | 63-71 | TYLPTNASL (SEQ ID NO: 30) |
| HER-2 | 106-114 | QLFEDNYAL (SEQ ID NO: 31) |
| HER-2 | 369-377 | KIFGSLAFL (SEQ ID NO: 7) |
| HER-2 | 435-443 | ILHNGAYSL (SEQ ID NO: 32) |
| HER-2 | 654-662 | IISAVVGIL (SEQ ID NO: 33) |
| HER-2 | 665-673 | VVLGVVFGI (SEQ ID NO: 34) |
| HER-2 | 689-697 | RLLQETELV (SEQ ID NO: 35) |
| HER-2 | 754-762 | VLRENTSPK (SEQ ID NO: 36) |
| HER-2 | 773-782 | VMAGVGSPYV (SEQ ID NO: 37) |
| HER-2 | 780-788 | PYVSRLLGI (SEQ ID NO: 38) |
| HER-2 | 789-797 | CLTSTVQLV (SEQ ID NO: 39) |
| HER-2 | 799-807 | QLMPYGCLL (SEQ ID NO: 40) |
| HER-2 | 835-842 | YLEDVRLV (SEQ ID NO: 41) |
| HER-2 | 851-859 | VLVKSPNHV (SEQ ID NO: 42) |
| HER-2 | 883-899 | KVPIKWMALESILRRRF (SEQ ID NO: 43) |
| HER-2 | 952-961 | YMIMVKCWMI (SEQ ID NO: 44) |
| HER-2 | 971-979 | ELVSEFSRM (SEQ ID NO: 45) |
| IL-13 receptor α2 | 345-354 | WLPFGFILI (SEQ ID NO: 8) |
| MAGE-1 | 102-112 | ITKKVADLVGF (SEQ ID NO: 46) |
| MAGE-1 | 135-143 | NYKHCFPEI (SEQ ID NO: 47) |
| MAGE-1 | 160-169 | KEADPTGHSY (SEQ ID NO: 48) |
| MAGE-1 | 161-169 | EADPTGHSY (SEQ ID NO: 4) |
| MAGE-1 | 230-238 | SAYGEPRKL (SEQ ID NO: 49) |
| MAGE-1 | 278-286 | KVLEYVIKV (SEQ ID NO: 50) |
| TRP-2 | 180-188 | SVYDFFVWL (SEQ ID NO: 5) |
| TRP-2 | 197-205 | LLGPGRPYR (SEQ ID NO: 51) |
| TRP-2 | 222-231 (TRP-2-int2 isoform) | EVISCKLIKR (SEQ ID NO: 52) |

TABLE 2-continued

Tumor Antigen Peptides

| Tumor antigen | Position in sequence | Peptide sequence |
|---|---|---|
| TRP-2 | 288-296 | SLDDYNHLV (SEQ ID NO: 53) |
| TRP-2 | 360-368 | TLDSQVMSL (SEQ ID NO: 54) |
| TRP-2 | 387-395 | ANDPIFVVL (SEQ ID NO: 55) |
| TRP-2 | 399-407 | LLYNATTNI (SEQ ID NO: 56) |
| TRP-2 | 403-411 | ATTNILEHY (SEQ ID NO: 57) |
| TRP-2 | 402-411 | NATTNILEHV (SEQ ID NO: 58) |
| TRP-2 | 455-463 | YAIDLPVSV (SEQ ID NO: 59) |

Antigenic peptides useful for loading DCs for vaccination are peptides that stimulate a T cell mediated immune response (e.g., a cytotoxic T cell response) by presentation to T cells on MHC molecules. Therefore, useful peptide epitopes of TRP-2, MAGE-1, gp100, AIM-2, IL-3 receptor α2, and HER-2, include portions of the amino acid sequences that bind to MHC molecules and are presented to T cells. Peptides that bind to MHC class I molecules are generally 8-10 amino acids in length. Peptides that bind to MHC class II molecules are generally 13 amino acids or longer (e.g., 13-17 amino acids long).

T cell epitopes can be identified by a number of different methods. Naturally processed MHC epitopes can be identified by mass spectrophotometric analysis of peptides eluted from antigen-loaded APC (e.g., APC that have taken up antigen, or that have been engineered to produce the protein intracellularly). After incubation at 37° C., cells are lysed in detergent and the MHC protein is purified (e.g., by affinity chromatography). Treatment of the purified MHC with a suitable chemical medium (e.g., under acidic conditions, e.g., by boiling in 10% acetic acid, as described in Sanchez et al., 94(9): 4626-4630, 1997) results in the elution of peptides from the MHC. This pool of peptides is separated and the profile compared with peptides from control APC treated in the same way. The peaks unique to the protein expressing/fed cells are analyzed (for example by mass spectrometry) and the peptide fragments identified. This protocol identifies peptides generated from a particular antigen by antigen processing, and provides a straightforward means of isolating these antigens.

Alternatively, epitopes are identified by screening a synthetic library of peptides which overlap and span the length of the antigen in an in vitro assay. For example, peptides which are 9 amino acids in length and which overlap by 5 amino acids may be used. The peptides are tested in an antigen presentation system that includes antigen presenting cells and T cells. T cell activation in the presence of APCs presenting the peptide can be measured (e.g., by measuring T cell proliferation or cytokine production) and compared to controls, to determine whether a particular epitope is recognized by the T cells.

The peptides can be modified to increase immunogenicity. For example, addition of dibasic amino acid residues (e.g., Arg-Arg, Arg-Lys, Lys-Arg, or Lys-Lys) to the N- and C-termini of peptides can render the peptides more potent immunogens.

The peptides can also include internal mutations that render them "superantigens" or "superagonists" for T cell stimulation. Superantigen peptides can be generated by screening T cells with a positional scanning synthetic peptide combinatorial library (PS-CSL) as described in Pinilla et al. Biotechniques, 13(6):901-5, 1992; Borras et al., J. Immunol. Methods, 267(1):79-97, 2002; U.S. Publication No. 2004/0072246; and Lustgarten et al., J. Immun. 176: 1796-1805, 2006. In some embodiments, a superagonist peptide is a peptide shown in Table 2, above, with one, two or three amino acid substitutions which render the peptide a more potent immunogen.

Antigenic peptides can be obtained by chemical synthesis using a commercially available automated peptide synthesizer. Chemically synthesized peptides can be precipitated and further purified, for example by high performance liquid chromatography (HPLC). Alternatively, the peptides can be obtained by recombinant methods using host cell and vector expression systems. "Synthetic peptides" includes peptides obtained by chemical synthesis in vitro as well as peptides obtained by recombinant expression. When tumor antigen peptides are obtained synthetically, they can be incubated with dendritic cells in higher concentrations (e.g., higher concentrations than would be present in a tumor antigen cell lysates, which includes an abundance of peptides from non-immunogenic, normal cellular proteins). This permits higher levels of MHC-mediated presentation of the tumor antigen peptide of interest and induction of a more potent and specific immune response, and one less likely to cause undesirable autoimmune reactivity against healthy non-cancerous cells.

Preparation of Antigen Presenting Cells

Antigen presenting cells (APC), such as dendritic cells (DC), suitable for administration to subjects (e.g., glioma patients) may be isolated or obtained from any tissue in which such cells are found, or may be otherwise cultured and provided. APC (e.g., DC) may be found, by way of example, in the bone marrow or PBMCs of a mammal., in the spleen of a mammal or in the skin of a mammal (i.e., Langerhan's cells, which possess certain qualities similar to that of DC, may be found in the skin). For instance, bone marrow may be harvested from a mammal and cultured in a medium that promotes the growth of DC. GM-CSF, IL-4 and/or other cytokines (e.g., TNF-α), growth factors and supplements may be included in this medium. After a suitable amount of time in culture in medium containing appropriate cytokines (e.g., suitable to expand and differentiate the DCs into mature DCs, e.g., 4, 6, 8, 10, 12, or 14 days), clusters of DC cultured in the presence of antigens of interest (e.g., in the presence of peptide epitopes of AIM-2, gp100, HER-2, MAGE-1, and TRP-2, or a combination of at least five of these peptides) and harvested for use in a cancer vaccine using standard techniques. Antigens (e.g., isolated or purified peptides, or synthetic peptides) can be added to cultures at a concentration of 1 µg/ml-50 µg/ml per antigen, e.g., 2, 5, 10, 20, 30, or 40 µg/ml per antigen.

In one exemplary method of preparing APC, APC are isolated from a subject (e.g., a human) according to the following exemplary procedure. Mononuclear cells are isolated from blood using leukapheresis (e.g., using a COBE Spectra Apheresis System). The mononuclear cells are allowed to become adherent by incubation in tissue culture flasks for 2 hours at 37° C. Nonadherent cells are removed by washing. Adherent cells are cultured in medium supplemented with granulocyte macrophage colony stimulating factor (GM-CSF) (800 units/ml, clinical grade, Immunex, Seattle, Wash.) and interleukin-4 (IL-4)(500 units/ml, R&D Systems, Minneapolis, Minn.) for five days. On day five, TNF-α is added to the culture medium for another 3-4 days. On day 8 or 9, cells are harvested and washed, and incubated with peptide antigens for 16-20 hours on a tissue rotator. Peptide antigens are added to the cultures at a concentration of ~10 µg/ml (per antigen).

Various other methods may be used to isolate the APCs, as would be recognized by one of skill in the art. DCs occur in low numbers in all tissues in which they reside, making isolation and enrichment of DCs a requirement. Any of a number of procedures entailing repetitive density gradient separation, fluorescence activated cell sorting techniques, positive selection, negative selection, or a combination thereof are routinely used to obtain enriched populations of isolated DCs. Guidance on such methods for isolating DCs can be found in O'Doherty, U. et al., J. Exp. Med., 178: 1067-1078, 1993; Young and Steinman, J. Exp. Med., 171: 1315-1332, 1990; Freudenthal and Steinman, Proc. Nat. Acad. Sci. USA, 57: 7698-7702, 1990; Macatonia et al., Immunol., 67: 285-289, 1989; Markowicz and Engleman, J. Clin. Invest., 85: 955-961, 1990; Mehta-Damani et al., J. Immunol., 153: 996-1003, 1994; and Thomas et al., J. Immunol., 151: 6840-6852, 1993. One method for isolating DCs from human peripheral blood is described in U.S. Pat. No. 5,643,786.

The dendritic cells prepared according to methods described herein present epitopes corresponding to the antigens at a higher average density than epitopes present on dendritic cells exposed to a tumor lysate (e.g., a neural tumor lysate). The relative density of one or more antigens on antigen presenting cells can be determined by both indirect and direct means. Primary immune response of naïve animals are roughly proportional to antigen density of antigen presenting cells (Bullock et al., J. Immunol., 170:1822-1829, 2003). Relative antigen density between two populations of antigen presenting cells can therefore be estimated by immunizing an animal with each population, isolating B or T cells, and monitoring the specific immune response against the specific antigen by, e.g., tetramer assays, ELISPOT, or quantitative PCR.

Relative antigen density can also be measured directly. In one method, the antigen presenting cells are stained with an antibody that binds specifically to the MHC-antigen complex, and the cells are then analyzed to determine the relative amount of antibody binding to each cell (see, e.g., Gonzalez et al., Proc. Natl. Acad. Sci. USA, 102:4824-4829, 2005). Exemplary methods to analyze antibody binding include flow cytometry and fluorescence activated cell sorting. The results of the analysis can be reported e.g., as the proportion of cells that are positive for staining for an individual MHC-antigen complex or the average relative amount of staining per cell. In some embodiments, a histogram of relative amount of staining per cell can be created.

In some embodiments, antigen density can be measured directly by direct analysis of the peptides bound to MHC, e.g., by mass spectrometry (see, e.g., Purcell and Gorman, Mol. Cell. Proteomics, 3:193-208, 2004). Typically, MHC-bound peptides are isolated by one of several methods. In one method, cell lysates of antigen presenting cells are analyzed, often following ultrafiltration to enrich for small peptides (see, e.g., Falk et al., J. Exp. Med., 174:425-434, 1991; Rotzxhke et al., Nature, 348:252-254, 1990). In another method, MHC-bound peptides are isolated directly fro the cell surface, e.g., by acid elution (see, e.g., Storkus et al., J. Immunother., 14:94-103, 1993; Storkus et al., J. Immunol., 151:3719-27, 1993). In another method, MHC-peptide complexes are immunoaffinity purified from antigen presenting cell lysates, and the MHC-bound peptides are then eluted by acid treatment (see, e.g., Falk et al., Nature, 351:290-296). Following isolation of MHC-bound peptides, the peptides are then analyzed by mass spectrometry, often following a separation step (e.g., liquid chromatography, capillary gel electrophoresis, or two-dimensional gel electrophoresis). The individual peptide antigens can be both identified and quantified using mass spectrometry to determine the relative average proportion of each antigen in a population of antigen presenting cells. In some methods, the relative amounts of a peptide in two populations of antigen presenting cells are compared using stable isotope labeling of one population, followed by mass spectrometry (see Lemmel et al., Nat. Biotechnol., 22:450-454, 2004).

Administration of Antigen Presenting Cells

The APC-based cancer vaccine may be delivered to a patient or test animal by any suitable delivery route, which can include injection, infusion, inoculation, direct surgical delivery, or any combination thereof. In some embodiments, the cancer vaccine is administered to a human in the deltoid region or axillary region. For example, the vaccine is administered into the axillary region as an intradermal injection. In other embodiments, the vaccine is administered intravenously.

An appropriate carrier for administering the cells may be selected by one of skill in the art by routine techniques. For example, the pharmaceutical carrier can be a buffered saline solution, e.g., cell culture media, and can include DMSO for preserving cell viability.

The quantity of APC appropriate for administration to a patient as a cancer vaccine to effect the methods of the present invention and the most convenient route of such administration may be based upon a variety of factors, as may the formulation of the vaccine itself. Some of these factors include the physical characteristics of the patient (e.g., age, weight, and sex), the physical characteristics of the tumor (e.g., location, size, rate of growth, and accessibility), and the extent to which other therapeutic methodologies (e.g., chemotherapy, and beam radiation therapy) are being implemented in connection with an overall treatment regimen. Notwithstanding the variety of factors one should consider in implementing the methods of the present invention to treat a disease condition, a mammal can be administered with from about $10^5$ to about $10^8$ APC (e.g., $10^7$ APC) in from about 0.05 mL to about 2 mL solution (e.g., saline) in a single administration. Additional administrations can be carried out, depending upon the above-described and other factors, such as the severity of tumor pathology. In one embodiment, from about one to about five administrations of about $10^6$ APC is performed at two-week intervals.

DC vaccination can be accompanied by other treatments. For example, a patient receiving DC vaccination may also be receiving chemotherapy, radiation, and/or surgical therapy concurrently. Methods of treating cancer using DC vaccination in conjunction with chemotherapy are described in Wheeler et al., US Pat. Pub. No. 2007/0020297. In some embodiments, a patient receiving DC vaccination has already received chemotherapy, radiation, and/or surgical treatment for the cancer. In one embodiment, a patient receiving DC vaccination is treated with a COX-2 inhibitor, as described in Yu and Akasaki, WO 2005/037995.

Immunological Testing

The antigen-specific cellular immune responses of vaccinated subjects can be monitored by a number of different assays, such as tetramer assays, ELISPOT, and quantitative PCR. The following sections provide examples of protocols for detecting responses with these techniques. Additional methods and protocols are available. See e.g., Current Protocols in Immunology, Coligan, J. et al., Eds., (John Wiley & Sons, Inc.; New York, N.Y.).

Tetramer Assay

Tetramers comprised of recombinant MHC molecules complexed with peptide can be used to identify populations of antigen-specific T cells. To detect T cells specific for antigens such as HER-2, gp100 and MAGE-1, fluorochrome labeled specific peptide tetramer complexes (e.g., phycoerythrin (PE)-tHLA) containing peptides from these antigens are synthesized and provided by Beckman Coulter (San Diego, Calif.). Specific CTL clone CD8 cells are resuspended at $10^5$ cells/50 µl FACS buffer (phosphate buffer plus 1% inactivated FCS buffer). Cells are incubated with 1 µl tHLA for 30 minutes at room temperature and incubation is continued for 30 minutes at 4° C. with 10 µl anti-CD8 mAb (Becton Dickinson, San Jose, Calif.). Cells are washed twice in 2 ml cold FACS buffer before analysis by FACS (Becton Dickinson).

ELISPOT Assay

ELISPOT assays can be used to detect cytokine secreting cells, e.g., to determine whether cells in a vaccinated patient secrete cytokine in response to antigen, thereby demonstrating whether antigen-specific responses have been elicited. ELISPOT assay kits are supplied from R & D Systems (Minneapolis, Minn.) and performed as described by the manufacturer's instructions. Responder (R) $1\times10^5$ patients' PBMC cells from before and after vaccination are plated in 96-well plates with nitrocellulose membrane inserts coated with capture Ab. Stimulator (S) cells (TAP-deficient T2 cells pulsed with antigen) are added at the R:S ratio of 1:1. After a 24-hour incubation, cells are removed by washing the plates 4 times. The detection Ab is added to each well. The plates are incubated at 4° C. overnight and the washing steps will be repeated. After a 2-hour incubation with streptavidin-AP, the plates are washed. Aliquots (100 µl) of BCIP/NBT chromogen are added to each well to develop the spots. The reaction is stopped after 60 min by washing with water. The spots are scanned and counted with computer-assisted image analysis (Cellular Technology Ltd, Cleveland, Ohio). When experimental values are significantly different from the mean number of spots against non-pulsed T2 cells (background values), as determined by a two-tailed Wilcoxon rank sum test, the background values are subtracted from the experimental values.

Quantitative PCR for IFN-γ Production

Quantitative PCR is another means for evaluating immune responses. To examine IFN-γ production in patients by quantitative PCR, cryopreserved PBMCs from patients' pre-vaccination and post-vaccinations samples and autologous dendritic cells are thawed in RPMI DC culture medium with 10% patient serum, washed and counted. PBMC are plated at $3\times10^6$ PBMCs in 2 ml of medium in 24-well plate; dendritic cells are plated at $1\times10^6$/ml and are pulsed 24 hour with 10 µg/ml tumor peptide in 2 ml in each well in 24 well plate. Dendritic cells are collected, washed, and counted, and diluted to $1\times10^6$/ml, and $3\times10^5$ (i.e., 300 µl solution) added to wells with PBMC (DC: PBMC=1:10). 2.3 µl IL-2 (300 IU/mL) is added every 3-4 days, and the cells are harvested between day 10 and day 13 after initiation of the culture. The harvested cells are then stimulated with tumor cells or autologous PBMC pulsed with 10 µg/ml tumor peptide for 4 hours at 37° C. On days 11-13, cultures are harvested, washed twice, then divided into four different wells, two wells using for control (without target); and another two wells CTL cocultured with tumor cells (1:1) if tumor cells are available. If tumor cells are not available, 10 µg/ml tumor lysate is added to CTL. After 4 hours of stimulation, the cells are collected, RNA extracted, and IFN-γ and CD8 mRNA expression evaluated with a thermocycler/fluorescence camera system. PCR amplification efficiency follows natural log progression, with linear regression analyses demonstrating correlation co-efficients in excess of 0.99. Based on empirical analysis, a one-cycle difference is interpreted to be a two-fold difference in mRNA quantity, and CD8-normalized IFN-γ quantities are determined. An increase of >1.5-fold in post-vaccine relative to pre-vaccine IFN-γ is the established standard for positive type I vaccine responsiveness.

In Vitro Induction of CTL in Patient-derived PBMCs

The following protocol can be used to produce antigen specific CTL in vitro from patient derived PBMC. To generate dendritic cells, the plastic adherent cells from PBMCs are cultured in AIM-V medium supplemented with recombinant human GM-CSF and recombinant human IL-4 at 37° C. in a humidified $CO_2$ (5%) incubator. Six days later, the immature dendritic cells in the cultures are stimulated with recombinant human TNF-α for maturation. Mature dendritic cells are then harvested on day 8, resuspended in PBS at $1\times10^6$ per mL with peptide (2 µg/mL), and incubated for 2 hours at 37° C. Autologous CD8+ T cells are enriched from PBMCs using magnetic microbeads (Miltenyi Biotech, Auburn, Calif.). CD8+ T cells ($2\times10^6$ per well) are cocultured with $2\times10^5$ per well peptide-pulsed dendritic cells in 2 mL/well of AIM-V medium supplemented with 5% human AB serum and 10 units/mL rhIL-7 (Cell Sciences) in each well of 24-well tissue culture plates. About 20 U/ml of IL-2 is added 24 h later at regular intervals, 2 days after each restimulation. On day 7, lymphocytes are restimulated with autologous dendritic cells pulsed with peptide in AIM-V medium supplemented with 5% human AB serum, rhIL-2, and rhIL-7 (10 units/mL each). About 20 U/ml of IL-2 is added 24 h later at regular intervals, 2 days after each restimulation. On the seventh day, after the three rounds of restimulation, cells are harvested and tested the activity of CTL. The stimulated CD8+ cultured cells (CTL) are co-cultured with T2 cells (a human TAP-deficient cell line) pulsed with 2 µg/ml Her-2, gp100, AIM-2, MAGE-1, or IL13 receptor α2 peptides. After 24 hours incubation, IFN-γ in the medium is measured by ELISA assay.

In Vivo Testing in Animal Models

Dendritic cell vaccination can be evaluated in animal models. Suitable models for brain cancers include injection models, in which cells of a tumor cell line are injected into the animal, and genetic models, in which tumors arise during development.

To evaluate dendritic cell vaccination in an animal model, functional dendritic cells are isolated from bone marrow derived cells of the animal and differentiated in vitro in the presence of cytokines, as detailed above. Mature dendritic cells are pulsed with tumor antigens (e.g., tumor antigens derived from the tumor cell line that will be implanted into the animal, or synthetic peptides corresponding to epitopes of those antigens). Animals are implanted with cells of the tumor cell line. After implantation, animals are vaccinated with antigen-pulsed dendritic cells one or more times. Survival and immune responsiveness is measured.

Pharmaceutical Compositions

In various embodiments, the present invention provides pharmaceutical compositions including a pharmaceutically acceptable excipient along with a therapeutically effective amount of the inventive vaccine comprising dendritic cells loaded with the antigens as described herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

In various embodiments, the pharmaceutical compositions according to the invention can be formulated for delivery via any route of administration. "Route of administration" can refer to any administration pathway known in the art, including, but not limited to, aerosol, nasal, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions can be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier can be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it can come in contact, meaning that it must not carry a risk of toxicity, irritation, allergic response, immunogenicity, or any other complication that excessively outweighs its therapeutic benefits.

The pharmaceutical compositions according to the invention can be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 21st edition, Williams & Wilkins PA, USA) (2005). In one embodiment, a therapeutically effective amount of the vaccine can comprise about $10^7$ tumor antigen-pulsed DC. In some embodiments, a therapeutically effective amount is an amount sufficient to reduce or halt tumor growth, and/or to increase survival of a patient.

Kits

The present invention is also directed to kits to treat cancers (e.g., neural cancers). The kits are useful for practicing the inventive method of treating cancer with a vaccine comprising dendritic cells loaded with the antigens as described herein. The kit is an assemblage of materials or components, including at least one of the inventive compositions. Thus, in some embodiments, the kit includes a set of peptides for preparing cells for vaccination. The kit can also include agents for preparing cells (e.g., cytokines for inducing differentiation of DC in vitro). The invention also provides kits containing a composition including a vaccine comprising dendritic cells (e.g., cryopreserved dendritic cells) loaded with the antigens as described herein.

The exact nature of the components configured in the inventive kit depends on its intended purpose. For example, some embodiments are configured for the purpose of treating neural cancers. Other embodiments are configured for the purpose of treating brain tumors. In one embodiment the brain tumor is a glioma. In another embodiment, the brain tumor is GBM. In another embodiment, the brain tumor is an astrocytoma. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use can be included in the kit. "Instructions for use" typically include a tangible expression describing the technique to be employed in using the components of the kit to effect a desired outcome, such as to treat cancer. For example, the instructions can comprise instructions to administer a vaccine comprising dendritic cells loaded with the antigens described herein to the patient. Instructions for use can also comprise instructions for repeated administrations of the vaccine; for example, administering the three doses of the vaccine in two week intervals.

Optionally, the kit also contains other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in cancer treatments or in vaccinations. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing for example, a vaccine comprising dendritic cells loaded with the antigens as described herein. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1

Human Studies

Phase I studies were initiated in two human patients to assess the safety and efficacy of an immunotherapy trial using peripheral blood dendritic cells to present brain tumor-specific markers to the patient's immune system. The details of these studies are described in Examples 2-8 below.

No significant adverse events (grade III/IV toxicity) have been noted in the patients thus far.

Example 2

Preparation of Autologous Dendritic Cells (DC)

Mononuclear cells were isolated from patients between days −28 to −14 using leukapheresis. The COBE Spectra Apheresis System was used to harvest the mononuclear cell layer. Leukapheresis yields $10^{10}$ peripheral blood mononuclear cells (PBMC). These cells were allowed to become adherent for two hours at 37° C. in a tissue culture flask and washed in HBSS. Briefly, PBMC were seeded at a density of $1.4 \times 10^6$ cells/cm$^2$ in 185-cm$^2$ culture flasks (Nunc, Roskilde, Denmark) and allowed to adhere for 2 h at 37° C. Non-adherent cells were removed by washing four times. Adherent cells were cultured in RPMI 1640 supplemented with GM-CSF (Berlex) and IL-4 (R&D systems) for 5 days. On day 5, 50 ng/ml clinical grade TNF-α (R&D systems) was added to the culture medium for another 3-4 days. On days 8-9, DCs were harvested and washed three times. Patients underwent the following tests within 7 days of Leukapheresis procedure:

ABO/Rh; Antibody Screen; Syphilis; HBsAg; HBcAb; anti-HCV; anti-HIV1, 2; anti-HTLV I/II; and HIV-1/HCV by Nucleic Acid Testing (NAT) (ABO/Rh does not need to be repeated within 7 days of Leukapheresis). Table 3 lists the names, manufacturers, methods, and an explanation of each of these tests.

TABLE 3

| TEST NAME ABBREV. | REAGENT MANUFACTURER | TEST METHOD | BRIEF EXPLANATION |
|---|---|---|---|
| Blood Group ABO/Rh | Gamma Biologicals, Inc. & Ortho Diagnostic Systems, Inc. a Johnson & Johnson Company | Olympus PK System PK7200 an Automated Pretransfusion Testing System & Manual Tube Test | Testing is necessary to determine if red blood cells possess or lack A and/or B and D blood group antigens. Agglutination is a positive test result indicating the presence of the corresponding antigen. Normal human red blood cells possessing antigens will agglutinate in the presence of antibody directed toward the antigens. |
| Blood Group ABO/Rh (Alternate) | Micro Typing Systems, Inc. | A/B/D Monoclonal Grouping Card A/B/D Reverse Monoclonal Grouping Card MTS Anti-IgG Card | |
| Antibody Screen Ab | Immucor, Inc. Norcross, GA | Capture-R Ready Screen | A qualitative test for the detection of unexpected blood group antibodies. Used to detect unexpected antibodies in the serum or plasma from donors. |
| Antibody Screen Ab (Alternate) | Micro Typing Systems, Inc. | MTS Anti-IgG Card | |
| Hepatitis B Surface Antigen HBsAg | Ortho-Clinical Diagnostics, Inc. Raritan, NJ | Antibody to Hepatitis B Surface Antigen (Murine Monoclonal): Peroxidase Conjugate ORTHO Antibody to HbsAg ELISA Test System 3 | This enzyme immunoassay (EIA) detects the presence of hepatitis B surface antigen (HbsAg) in human serum or plasma. |
| Human Immunodeficiency Virus Types 1 and 2 HIV-1/2 | Bio-Rad Laboratories, Redmond, WA | Human Immunodeficiency Virus Types 1 and 2 (Synthetic Peptide): Genetic Systems HIV-1/HIV-2 Peptide EIA | This enzyme-linked immunoassay (EIA) allows simultaneous detection of antibodies to HIV-1 and HIV-2. It does not discriminate between HIV-1 and HIV-2 reactivity. |
| Syphilis Serology SYP | Olympus America Inc., Melville, NY | Olympus PK TP System | This test is intended for the qualitative detection of *Treponema pallidum* antibodies in human serum or plasma. This agglutination test utilizes fixed chicken erythrocytes sensitized with components of the pathogenic *T. pallidum* to detect antibodies in specimens. |

TABLE 3-continued

| TEST NAME ABBREV. | REAGENT MANUFACTURER | TEST METHOD | BRIEF EXPLANATION |
|---|---|---|---|
| Syphilis Serology (Alternate) | Immucor, Inc., Norcross, GA | Capture-S | |
| Human T-Lymphotrophic Virus Type I and Type II HTLV-I/II | BIOMERIEUX, Inc., Durham, NC | Human T-Lymphotrophic Virus Type I and Type II (HTLV-I/II): Vironostika HTLV-I/II Microelisa System | This enzyme-linked immunoassay (EIA) detects antibodies to HTLV-I and antibodies to HTLV-II. |
| Hepatitis C Virus Encoded Antigen HCV | ORTHO Clinical Diagnostics, Inc., Raritan, NJ | Hepatitis C Virus Encoded Antigen (Recombinant c22-3, C200 and NS5) ORTHO HCV Version 3.0 ELISA Test System | This enzyme immunoassay utilizes recombinant antigens to detect antibody to Hepatitis C virus (HCV). Presence of this antibody indicates past or present HCV infection, or possibly a carrier state, but does not substantiate infectivity nor immunity. The anti-HCV EIA 3.0 version test includes NS5, c200, and c22-3 recombinant antigens. The NS antigen is derived from the polymerase of the HCV genome and allows antibody detection of a greater number of HCV epitopes. |
| Nucleic Acid Testing (NAT) Procleix HIV-1/HCV RNA NAT | Gen-Probe Incorporation, San Diego, CA | Procleix HIV-1/HCV Assay | This assay utilizes target amplification nucleic acid probe technology for the detection of HIV-1 and/or HCV RNA. The screen assay is referred to as "multiplex testing" which does not discriminate between HIV-1 and HCV RNA. Specimens found to be reactive upon multiplex testing are then tested in HIV-1 and HCV Discriminatory Assays (dHIV and dHCV assays) to determine if they are reactive for HIV, HCV, both or neither. All assays have a chemiluminescent signal produced by a hybridized probe, which is measured by a luminometer and reported as Relative Light Units (RLU). |

Example 3

Preparation of Vaccines

Human leukocyte antigen A1 (HLA-A1, or A1) and human leukocyte antigen A2 (HLA-A2, or A2) positive patients with recurrent brain stem glioma or glioblastoma were identified. Dendritic cells, prepared as described in Example 2, were pulsed with peptide epitopes of tumor antigens that bind to HLA-A1 or HLA-A2, to load the cells with the antigens, prior to frozen storage. The peptide epitopes were from the following tumor antigens: MAGE-1, HER-2, AIM-2, TRP-2, gp100, and interleukin-13 receptor α2. The sequences of these peptide epitopes used in these studies are listed in Table 4, below. Other epitopes for these antigens can also be used.

TABLE 4

Tumor Antigen Peptides

| Antigen | HLA-A1 epitope | Antigen | HLA-A2 epitope |
|---|---|---|---|
| AIM-2 | RSDSGQQARY (SEQ ID NO: 3) | TRP-2 | SVYDFFVWL (SEQ ID NO: 5) |
| MAGE-1 | EADPTGHSY (SEQ ID NO: 4) | GP100 | ITDQVPFSV (SEQ ID NO: 6) |
| | | HER-2 | KIFGSLAFL (SEQ ID NO: 7) |
| | | IL-13R α2 | WLPFGFILI (SEQ ID NO: 8) |

Tumor antigen epitopes were purchased from Clinalfa (Läufelfingen, Switzerland).

On the day prior to immunization, days 8-9 DC cultures were washed three times in dPBS, resuspended at $10^6$ cells/ml in complete media and then coincubated with tumor associated antigen peptides (10 μg/ml per antigen, reconstituted in 10% DMSO). The dendritic cells were incubated with the peptides at 37°/5% $CO_2$ for 16-20 hours on a tissue rotator to facilitate interaction.

Mature (d8-9) DC were frozen as follows: DC are resuspended in cryo tubes at various concentrations ($1 \times 10^7$ cells per ml in autologous freezing medium (10% DMSO and 90% autologous serum), then immediately transferred to 1.8 ml cryo tubes (cryo tube vials, Nunc, Brand Products, Roskilde, Denmark), slowly frozen to −80° C. by using a cryo freezing container (Nalgene cryo 1° C. freezing container, rate of cooling −1° C./min (Fisher Scientific, CA)) and finally transferred into the gas phase of liquid nitrogen until use.

Sterility testing was conducted to confirm suitability for use. To test sterility, APC were cultured in RPMI medium, 10% heat-inactivated human AB serum, and 1% Gentamicin "GIBCO". Purchased Human AB serum was heat inactivated to 56° C. for one hour prior to preparation of complete medium. Each batch of complete medium was prepared on the day of each blood draw and sterile filtered (0.22 μm filter; Nalgene) prior to use. Complete media was refrigerated during the 9 day APC culture period. On day 2 of the APC culture, an aliquot of spent culture media was removed and subjected to sterility testing using BacT/Alert system with aerobic and anaerobic bottles that are cultured for 14 days total in an automated system.

In addition, a gram stain, sterile culture, mycoplasma, and LAL endotoxin assays are performed on the final product before the administration to the patient.

Acceptance Criteria for Test Article: 5 Eu/ml/kg of patient (endotoxin); no growth in sterility cultures; no bacteria seen by gram staining, hybridization control positive, water control negative, and the vaccine product exhibiting no sustained logarithmic increase in fluorescence intensity for mycoplasma QPCR.

Example 4

Protocol for Administering the Vaccine

For immunization, the patient received $10^7$ tumor antigen-pulsed dendritic cells, intradermally in 1 ml autologous freezing media in the axillary region. The patient was monitored for two hours post-immunization. Patients can receive pretreatment with 50 mg diphenhydramine and 650 mg of Tylenol, both orally (only as needed to treat symptoms or for the prevention of the recurrence of any prior study-agent-associated symptoms). The schedule of vaccine administration, and pre- and post-vaccine testing is shown in Table 5. The schedule of blood draws for vaccine preparation and testing is shown in Table 6.

TABLE 5

Vaccination and Immunological Testing Schedule

| Day | Events |
| --- | --- |
| −28 to −14 | A patient is screened and informed consent is obtained. MRI, Blood draw for serum (to supplement freezing medium), Immunological tests (pretreatment), Leukapheresis and preparation of dendritic cells is performed. |
| 0 | TAA-pulsed APC vaccination (1st). |
| 14 | TAA-pulsed APC vaccination (#2). |
| 28 | TAA-pulsed APC vaccination (#3). |
| 56 | Immunological tests, MRI, AE assessment, blood tests, targeted exam, Karnofsky (week 10), MRI every 2 months, are performed. |
| 180 | Immunological tests are performed (month 4). |

TABLE 6

Specific Blood Draw and Volume Schedule

| Day | Event | Vol. |
| --- | --- | --- |
| −28 | Blood draw for serum + DC's | 100 ml |
| −28 | Immunological tests | 70 ml |
| 56 | Immunological tests | 70 ml |
| 180 | Immunological tests | 70 ml |

Example 5

Screening and Baseline Evaluations

The following clinical and laboratory evaluations occur within days −28 to −9 unless otherwise noted.

Objective Signs and Symptoms: Includes vital signs (blood pressure, pulse, temperature and respirations), and weight. (Screening and repeat Day 0.)

History and Review of Systems: Screening and Review of Systems on Day −28 to −9, repeated Neurological exam on Day 0.

Karnofsky Performance Status (Screening)

KARNOFSKY INDEX:
  100 Normal; no complaints; no evidence of disease.
  90 Able to carry on normal activity; minor signs or symptoms.
  80 Normal activity with effort; some signs or symptoms.
  70 Cares for self; unable to carry on normal activity or to do active work.
  60 Requires occasional assistance; able to care for most needs.
  50 Requires considerable assistance; able to care for most needs.
  40 Disabled; requires special care and assistance.
  30 Severely disabled; hospitalization necessary; active supportive treatment necessary.
  20 Very sick; hospitalization necessary; active supportive treatment necessary.
  10 Moribund; rapidly progressing fatal process.
  0 Dead.

MRI of Brain with and without contrast

Urinalysis: Normal routine urinalysis

Serum Chemistries: Includes uric acid, calcium, phosphorous, magnesium, amylase, triglycerides, transaminases (AST, ALT), alkaline phosphatase, LDH, total bilirubin, BUN, creatinine, albumin, total protein, electrolytes, glucose (Screening), ANA, and TSH.

Hematology: Complete blood count (CBC), differential, platelets, and coagulation tests should include PT (Prothrombin Time) and PTT (Partial Thromboplastin Time). PT and PTT will be done at screening only and are repeated if clinically indicated.

Example 6

Interval Evaluations

Objective Signs and Symptoms: vital signs (blood pressure, pulse, temperature and respiration) and weight will be done.

Review of Systems: Neurological exam will be done on Study Days (i.e., days when the patient sees a physician).

Karnofsky Performance Status are done on Study Days.

Serum Chemistries Include uric acid, calcium phosphorous, magnesium, amylase, triglycerides, transaminases (AST, ALT), alkaline phosphatase, LDH, total bilirubin, BUN, creatinine, albumin, total protein, electrolytes glucose, ANA, and TSH.

Hematology: Complete blood count (CBC), differential platelets and coagulation tests should include PT (Prothrombin time) and PTT (Partial Thromboplastin time).

MRI of brain with and without contrast (q2 months).

Example 7

Vaccination Modification and General Management of Toxicities

A Table for Grading Severity of Adverse Experience (AE) is used to achieve consistency in response to drug/treatment toxicities. Toxicities are graded on the NIH Common Toxicity Criteria, a 1-4 basis scale. If a toxicity is experienced, the treatment level or dose is modified (if applicable) as outlined below according to the grade of toxicity observed. AEs related to neurological deficits or post-vaccination therapy due to tumor progression. All SAEs will be reported until survival.

For any Grade 1 toxicity there will be no dose modification.

If a Grade 2 toxicity develops, the patient will not receive a planned subsequent vaccine injection until values return to Grade 1 or less for at least one week.

All vaccine administrations will cease for any patient who experiences any of the following outcomes within one month following any vaccine injection: any grade 3 or 4 adverse event; a grade 2 (or greater) allergic adverse event; or a grade 2 (or greater) neurologic adverse event not readily attributable to the tumor.

Symptomatic therapy such as analgesics or other helpful therapy can be administered if deemed necessary.

Example 8

Primary Safety and Efficacy Analyses

The primary safety outcome is number of Grade 3 or 4 toxicities. Safety outcomes are followed over a period of one year following the last study agent dose administration.

The primary endpoint is survival time (from date of vaccination to date of death or the last date known alive if death was not observed).

The secondary endpoints of progression free survival after vaccination are measured radiologically with MRI scan of the brain with and without gadolinium. Patients will undergo an MRI every two months after the last study agent administration Standardized response criteria as outlined below have been adopted.

Complete Response: Complete disappearance of all tumor on MRI with a stable or improving neurologic examination.

Partial Response: Greater than or equal to 50% reduction in tumor size on volumetric MRI scan with a stable or improving neurologic examination.

Progressive Disease or Recurrent Disease: Progressive neurologic abnormalities or a new or greater than 25% increase in the volume of the gadolinium-enhancing tumor by MRI scan.

Stable Disease: A patient whose clinical status and MRI volumetrics do not meet the criteria for partial response or progressive disease.

Dose limiting toxicities are followed for one month after the last study agent administration.

Example 9

In Vivo Testing in an Animal Model

The following in vivo animal experiments demonstrate the efficacy of a dendritic cell vaccine. To isolate functional dendritic cells (DC), cells were harvested from rat bone marrow. Bone marrow suspensions were supplemented with GM-CSF (50 ng/ml) and IL-4 (100 ng/ml) for 8 days, which have been shown to induce the differentiation of functional dendritic cells. Mature dendritic cells from culture were positively identified based on their surface antigen expression via flow cytometry (FACS). Dendritic cells were positively identified based on their expression of MHC Class II, MHC Class I, CD11b/c, and Thy1.1, and their lack of CD3 and CD8 expression. Cultures enriched for dendritic cells were pulsed (co-cultured) overnight with acid eluted tumor peptides from syngeneic 9L rat glioma cells.

In these animal experiments, 9L glioma cells were stereotactically implanted into the right cerebral hemisphere of Fischer 344 rats. One week after tumor implantation, animals were injected subcutaneously with $5 \times 10^5$ 9L peptide-pulsed dendritic cells, unpulsed dendritic cells or control media. Three weekly injections were given. Animals in each of the treatment groups were followed for survival. The results revealed that a significantly higher percentage of animals treated with 9L peptide-pulsed dendritic cells were still surviving at 20 days (10/12=83%) compared to those treated with unpulsed cells (2/6=33%) or untreated animals (3/10=30%).

Example 10

Enhanced Immune Responsiveness to T cell Epitopes with Dibasic Motifs

In studies using mouse lysozyme-M (ML-M) as a model self Ag, it was observed that mice of diverse MHC haplotypes were tolerant to native (unmutated) ML-M and peptide forms of certain T cell epitopes. It was hypothesized that tolerance to a given epitope was not an inherent structural characteristic, but was attributable in part to inefficient processing of the epitope, owing either to the absence of a proteolytic cleavage site adjacent to that determinant, or to the inaccessibility to the proteolytic enzyme(s) of an existing cleavage site within that region of the molecule. In either case, the provision of a new proteolytic cleavage site adjacent to a cryptic determinant may permit scission of the peptide at that site, making the previously cryptic epitope region available for binding to the appropriate MHC molecule, and lead to presentation to specific T cells of that determinant as a neodominant epitope on the APC surface. To test this proposition, a dibasic motif, consisting of two contiguous basic amino acid residues, e.g., arg-arg (RR) or arg-lys (RK), was used.

The targeted regions within ML-M included residues 19-31, which contain cryptic epitopes for mice of the H-$2^k$ haplotype, shown in Table 7.

TABLE 7

| Creation of Dibasic Motifs in Flanking Region of a Defined Cryptic Epitope Within ML-M | | | | |
|---|---|---|---|---|
| | ML-M | | | |
| Target Epitope[a] | Dominant Epitope for Mouse Strain (H-2)[a] | ML-M T cell epitope | Dibasic Site | Resulting Dibasic Motif |
| 19-30 | C3H/HeJ (H-$2^k$) | RR-GYYGVSLADWVC (SEQ ID NO: 60) | 18 | RR |
| 19-30 | C3H/HeJ (H-$2^k$) | GYYGVSLADWVC-RR (SEQ ID NO: 61) | 31 | RR |
| 19-30 | C3H/HeJ (H-$2^k$) | RR-GYYGVSLADWVC-RR (SEQ ID NO: 62) | 18 + 31 | RR-RR |

Groups of mice (3 per group) were immunized by IV injection of each peptide (ML-M, p19-30, or 18R31R. T cells were isolated from lymph node of the animals. Single cells in 96 well plates were recalled with each of the peptides and response to each of the peptides was measured. Interestingly, C3H mice challenged with ML-M failed to respond to the immunogen and to various peptides of this self lysozyme, including peptide 19-31, whereas immunization with RR-p18-31-RR raised a potent T cell response to this altered lysozyme as well as to p19-30 (FIG. 1). These results demonstrate that the dibasic site RR/KK mediated an efficient processing of the epitope 19-30, leading to activation of specific T cells. Furthermore, the T cells primed by RR-p18-31-RR could be restimulated in vitro with RR -p18-31-RR, but not by ML-M or peptides from other regions of ML-M. These results further confirmed the efficient presentation by the APC of epitope 19-30, but not ML-M to specific T cells, and also demonstrated the T cell cross-reactivity with synthetic p19-30.

Studies related to these studies with ML-M are performed with HER-2. HER-2/neu is a self-antigen expressed by tumors and nonmalignant epithelial tissues. The possibility of self-tolerance to HER-2/neu-derived epitopes has raised questions concerning their utility in antitumor immunotherapy. Altered HER-2/neu peptide ligands capable of eliciting enhanced immunity to tumor-associated HER-2/neu epitopes may circumvent this problem. The human CTL peptide HER-2/neu (435-443) modified with RR or RK dibasic motifs is an example of an altered peptide ligand of HER2.

The following exemplary dibasic-modified forms of HER2 peptides are obtained from Macromolecular Resources and Global Peptide Services: hHER-2($9_{435}$) (RRILHNGAYSLRR) (SEQ ID NO:1) and RRKIFGSLAFLRR (SEQ ID NO:2).

Murine In Vivo Lymphocyte Proliferation Assay

To test immunogenicity in an animal model, mice are immunized s.c. either altered hHER-2 peptide or with a peptide of hHER-2 (1 mg/ml each), each emulsified in complete Freunds adjuvant (CFA; Invitrogen Life Technologies) (1:1, v/v). After 8 or 9 days, the draining lymph node cells ($5\times10^5$/well) of these mice are tested in a proliferation assays using the appropriate peptides. Purified protein derivative (PPD) (Mycos Research) is used as a positive control. The incorporation of radioactivity ([$^3$H]thymidine) is assayed by liquid scintillation counting. The results will be expressed either as counts per minute (cpm) or as a stimulation index (stimulation index=cpm with recall antigen/cpm with cells in medium alone).

In Vitro Cell Proliferation Assay Using Paraformaldehyde (PF)-fixed APC

Cell proliferation is tested in vitro using the following assay. Briefly, DC from PBMC are used as APC. APC are fixed by incubation with 0.5% paraformaldehyde (PF; Sigma-Aldrich) for 10 min at room temperature either before or after pulsing with antigen. Naive unfixed APC are used as a control for fixed APC. Antigen-primed T cells are purified from LNC and spleen of antigen-challenged mice using a nylon wool column (Polysciences), and then cultured ($1.5\times10^5$/well) with fixed/unfixed APC ($3.75\times10^5$/well). APC plus T cells without Ag, and T cells with Ag only (no APC) serve as additional controls. The results are expressed as cpm or stimulation index, as described above.

T Cell ATP Release Function Assay

DC are pulsed with peptides for 16-20 hours, then incubated with CD4/CD8 T cells overnight and analyzed with an ATP releasing T cell proliferation assay. Table 8 lists the correlation of ATP levels with immune responsiveness, and suitability for a vaccine.

TABLE 8

| Correlation of ATP Level with Immune Response | | |
|---|---|---|
| ATP Range (ng/mL) | Immune Response | Interpretation Vaccine |
| 225 | Low | − |
| 226-524 | moderate | +/− |
| 525 | strong | + |

Measurement of the Cytokine Levels

LNC of antigen-primed mice are restimulated with antigen in vitro for 48 h. Thereafter, the culture supernatants are collected and assayed by ELISA using kits for IFN-γ and IL-4 (BioSource International). The absorbance is read at 450 nm using MicroElisa autoreader (Molecular Devices). The results are expressed as Δpg/ml (=cytokine secreted by LNC with Ag—cytokine in medium control). The Th1/Th2 ratio is derived from the levels of IFN-γ/IL-4, respectively.

Determination of the Serum Levels of Ag-specific Abs

The level of antibodies (total IgG, IgG1, and IgG2a) in sera is tested at different dilutions and detected by ELISA using different antigen (0.1 μg/well of a high binding ELISA plate (Greiner Bioscience)) and the appropriate HRP-conjugated secondary Ab against total Ig, or Ab specific for the IgG1 or IgG2a isotype (BD Pharmingen) (1:1000) following standard procedures. The results will be expressed as OD (450 nm) units.

Example 11

IFN-γ Production of Altered Peptide Ligands (APL)-specific CTLs

Figure 2A:
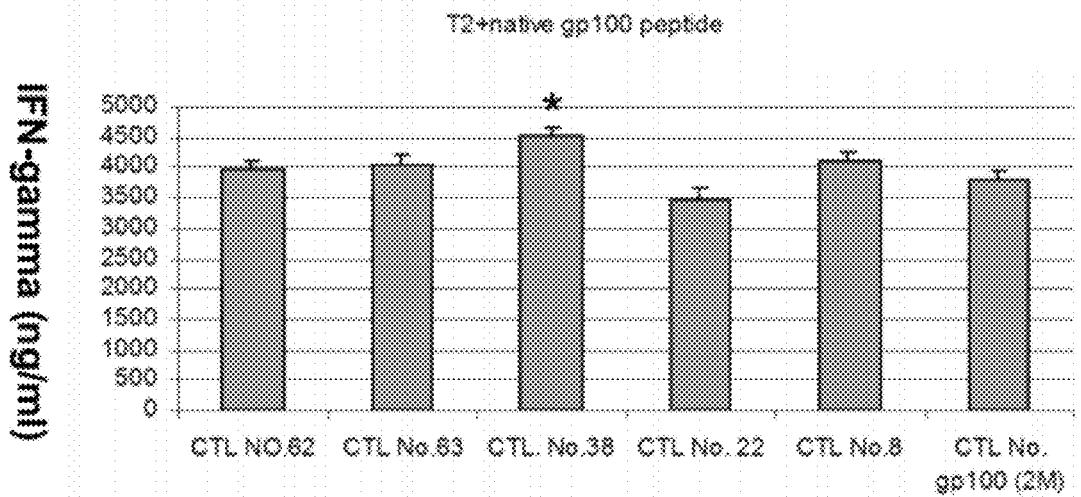
FIGS. 2A and 2B are bar graphs that show IFN-γ levels after in vitro induction of CTL in patient-derived PBMCs with dendritic cells pulsed with gp100(2M) or superagonist gp100 peptides in accordance with an embodiment of the present invention in two separate patients.
Figure 2B:
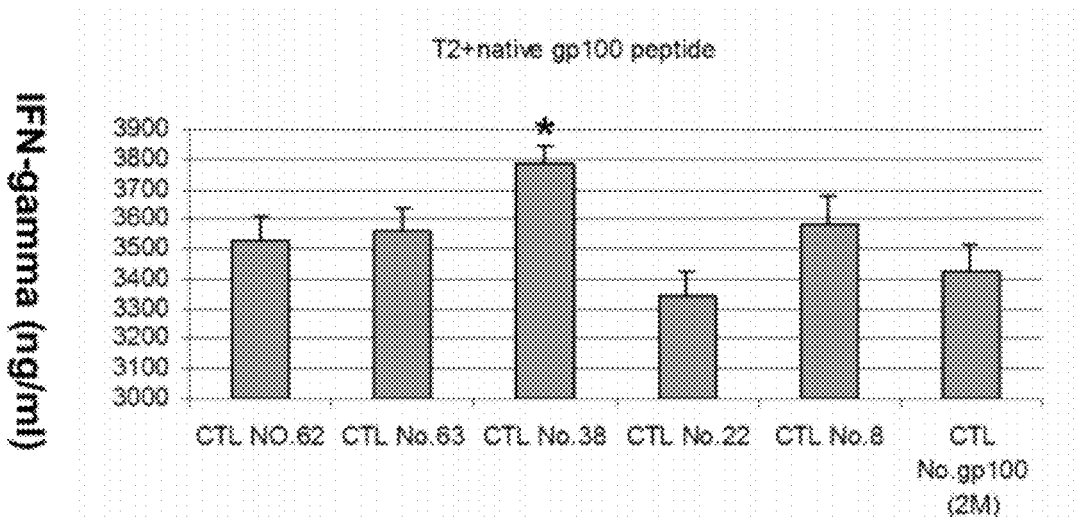
Figure 3A:
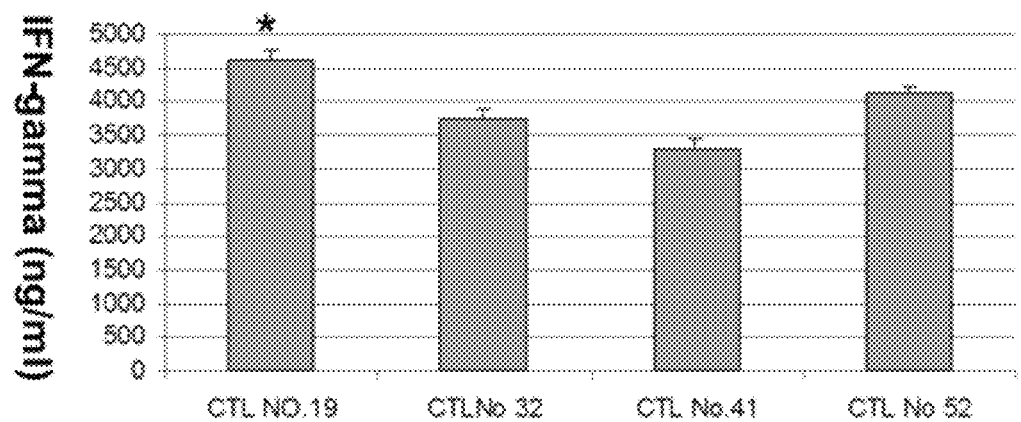
FIGS. 3A and 3B are bar graphs that show IFN-γ levels after in vitro induction of CTL in patient-derived PBMCs with native or superagonist Her-2 peptides in accordance with an embodiment of the present invention in two different patients.
Figure 3B:
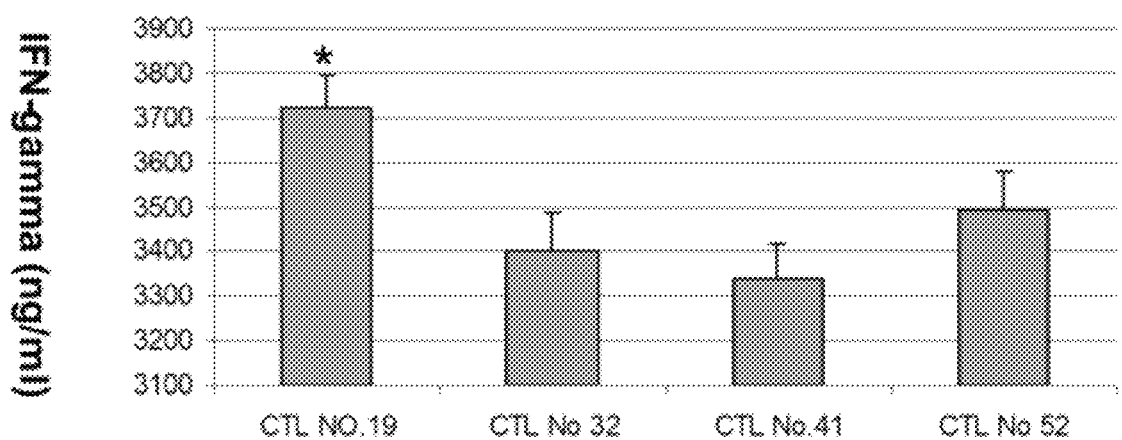

The immunogenicity of the APLs (also referred to herein as superagonist epitopes) in two HLA-A*0201 GBM patients were tested to determine the capacity of prime CTL responses in vitro. The results of these experiments are depicted in FIGS. 2 and 3.

For the gp100 APLs, among six different CTLs stimulated by six different peptides, No. 38 showed the highest IFN-γ level when targeting T2 pulsed with gp100 native peptide in both patients. There was a significant difference (P<0.05) when CTL No. 38 was compared with CTL generated by the gp100 (2M) peptide.

For the Her-2 APLs, among four different CTLs stimulated by four different peptides, No. 19 showed the highest IFN-γ level when targeting T2 pulsed Her-2 native peptide in both patients. There was a significant difference (P<0.05) when CTL No. 19 was compared with CTL generated by CTL No. 52 and CTL generated by Her-2 native peptide. In conclusion, among the tested peptides, No. 38 and No. 19 are the best superagonists.

Tables 9 and 10 list the altered peptide ligand (i.e., superagonist epitope) sequences of gp-100 and Her-2, respectively. The bolded letters indicate the amino acid that is substituted in place of the native amino acid residue. gp100 (2M) is an analog of the native gp100 with a replacement of the amino acid T with M. The native gp100 peptide sequence is as follows: ITDQVPFSV (SEQ ID NO:6). Peptide No. 52 is a native HER-2 peptide and not an altered peptide. The peptides were dissolved in 5% DMSO at 2 mg/ml and stored at −20° C. until taken out for use.

TABLE 9

Amino acid sequences of gp100 APL

| | | |
|---|---|---|
| gp100 (2M) | H- I T D Q V P F S V -NH₂ | SEQ ID NO: 6 |
| No. 8 | H- F L D Q V P Y S V -NH₂ | SEQ ID NO: 63 |
| No. 22 | H- F M D Q V P Y S V -NH₂ | SEQ ID NO: 64 |
| No. 38 | H- Y M D Q V P Y S V -NH₂ | SEQ ID NO: 65 |
| No. 62 | H- I L D Q V P F S V -NH₂ | SEQ ID NO: 66 |
| No. 63 | H- I M D Q V P F S V -NH₂ | SEQ ID NO: 67 |

TABLE 10

Amino acid sequences of HER-2 APL

| | | | |
|---|---|---|---|
| No. 19 | H- F M A N V A I P H L -NH₂ | SEQ ID NO: 68 | cp1 |
| No. 32 | H- F M H N V P I P Y L -NH₂ | SEQ ID NO: 69 | cp14 |
| No. 41 | H- F Y A N V P S P H L -NH₂ | SEQ ID NO: 70 | cp23 |
| No. 52 | H- V M A G V G S P Y V -NH₂ | SEQ ID NO: 71 | native, C-terminal amide |

Example 12

In Vitro Induction of CTL in Patient-Derived PBMCs and Stimulation with Altered Peptide Ligands (Superagonist Peptides)

The following assays were used to further evaluate immune responses to the altered peptide ligands described in Example 11. To generate dendritic cells, plastic-adherent cells from human PBMCs were cultured in AIM-V medium supplemented with recombinant human GM-CSF and recombinant human IL-4 at 37° C. in a humidified $CO_2$ (5%) incubator. Six days later, the immature dendritic cells were stimulated with recombinant human TNF-α for maturation. Mature dendritic cells were then harvested on day 8, resuspended in PBS at $1 \times 10^6$ per mL with peptide (2 µg/mL), and incubated for 2 hours at 37° C.

Autologous CD8+ T cells were enriched from PBMCs using magnetic microbeads (Miltenyi Biotech, Auburn, Calif.). CD8+ T cells ($2 \times 10^6$ per well) were cocultured with $2 \times 10^5$ per well peptide-pulsed dendritic cells in 2 mL/well of AIM-V medium supplemented with 5% human AB serum and 10 units/mL rhIL-7 (Cell Sciences) in each well of 24-well tissue culture plates. The gp100 and Her-2 peptides used for pulsing the dendritic cells are described in Example 11. On the next day and then every 3 days, 300 IU/ml IL-2 was added to the medium. On day 7, lymphocytes were restimulated with autologous dendritic cells pulsed with peptide in AIM-V medium supplemented with 5% human AB serum, rhIL-2, and rhIL-7 (10 units/mL each).

CTL Co-Culture with GBM Tumor Cells

Figure 4:
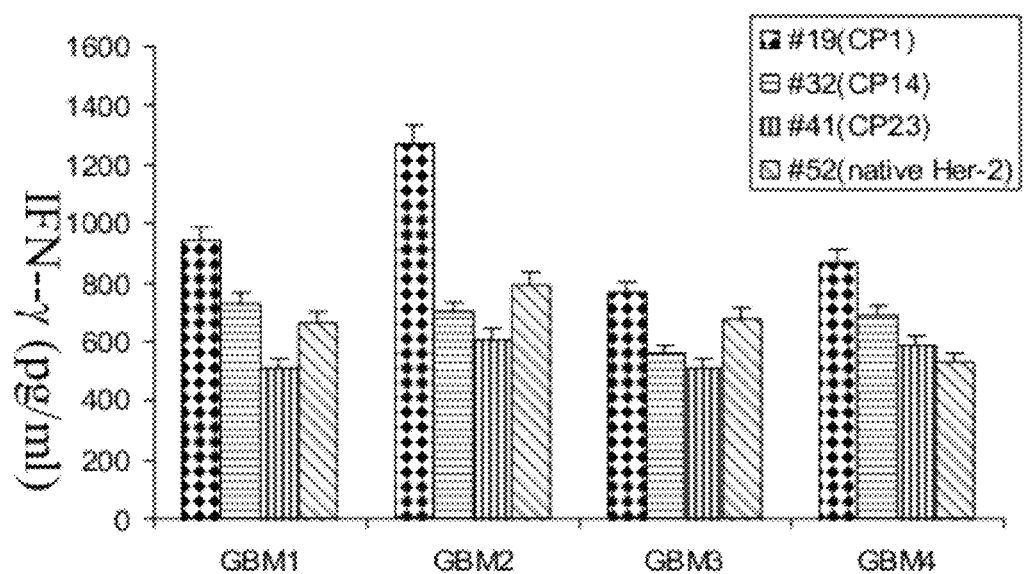
FIG. 4 is a bar graph that shows IFN-γ levels produced by CTL after in vitro induction of the CTL in patient-derived PBMCs with native (no. 52) or altered Her-2 peptides (nos. 19, 32, and 41), as measured by ELISA. CTL were cocultured with Her-2 positive, gp100 positive cell lines.
Figure 6:
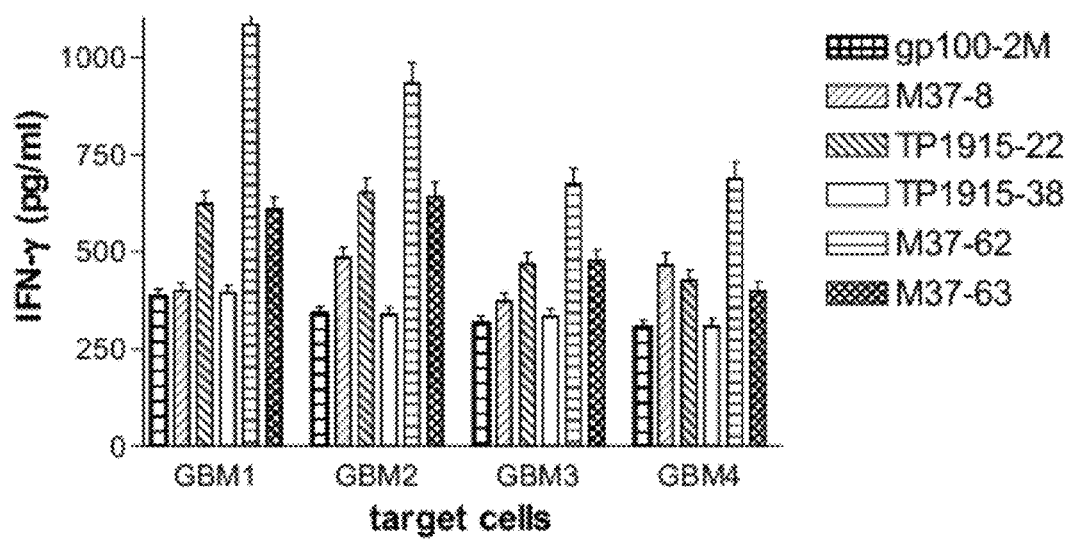
FIG. 6 is a bar graph that shows IFN-γ levels produced by CTL after in vitro induction of the CTL in patient-derived PBMCs with a native (no. 2M) or altered gp100 peptides (nos. 8, 22, 38, 62, and 63), as measured by ELISA. CTL were cocultured with Her-2 positive, gp100 positive cell lines.

After three cycles of stimulation, on day 20, the CD8+ cultured cells (CTL) were co-cultured with four GBM cell lines, which are both HLA-A2 and HER-2, gp100 positive cell lines. After a 24 hour incubation, IFN-γ in the medium was measured by ELISA assay. The data are shown in FIG. 4 and FIG. 6.

ELISPOT Assays

Figure 5:
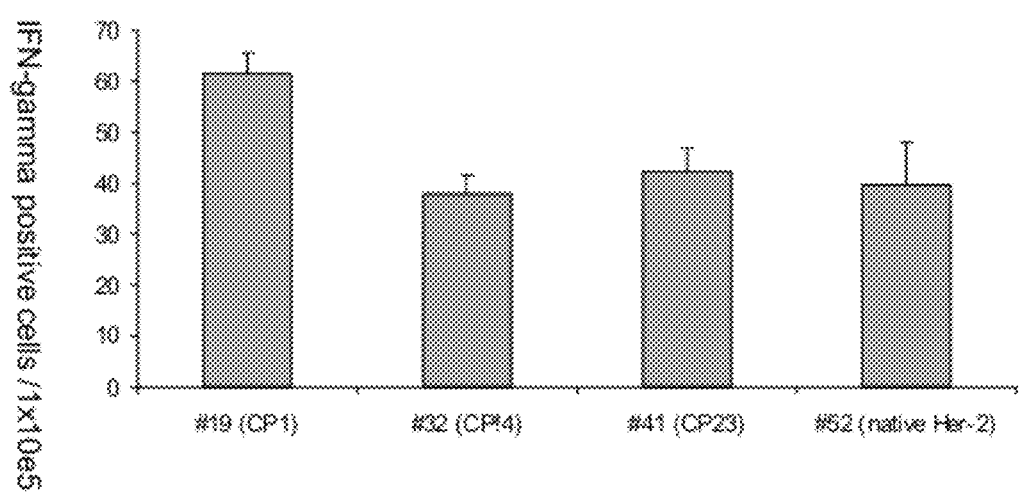
FIG. 5 is a bar graph that shows numbers of IFN-γ positive cells, as measured by ELISPOT analysis of CTL generated against Her-2 peptide nos. 19, 32, 41, and 52. For the ELISPOT assays, CTL were incubated with T2 cells pulsed with a HER-2 native peptide.
Figure 7:
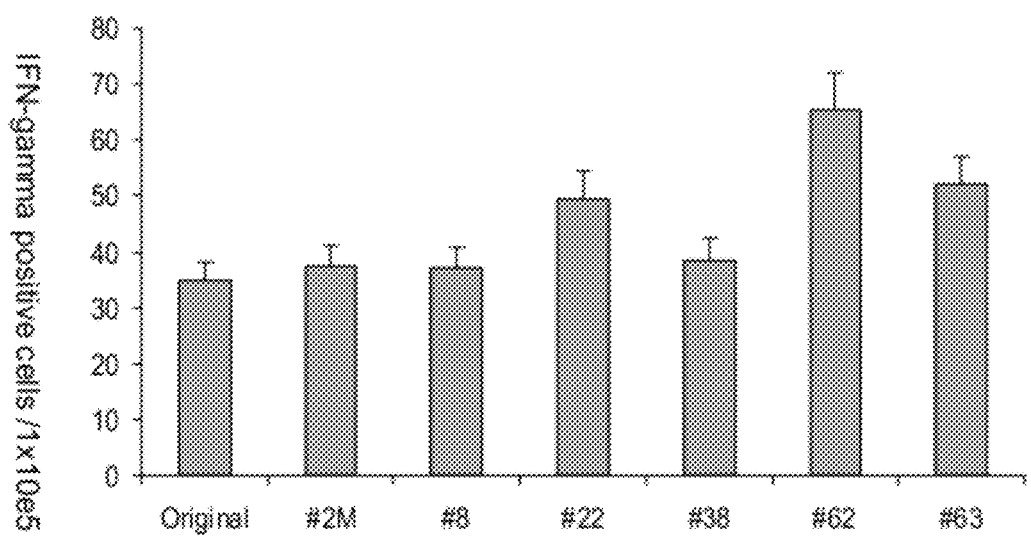
FIG. 7 is a is a bar graph that shows numbers of IFN-γ positive cells, as measured by ELISPOT analysis of CTL generated against gp100 peptide nos. 2M, 8, 22, 38, 62, and 63. For the ELISPOT assays, CTL were incubated with T2 cells pulsed with a gp100 native peptide.

ELISPOT assays were performed with kits (R & D Systems, Minneapolis, Minn.) according to the manufacturer's instructions. After three cycles of stimulation, on day 20, the CD8+ cultured cells (CTL) were plated in 96-well plates with nitrocellulose membrane inserts coated with capture antibody (Ab). Target cells (T2 pulsed HER-2 native peptide for FIG. 5 or T2 pulsed gp100 native peptide for FIG. 7) were added at the CTL: target ratio of 1:1. After a 24 hour incubation, cells were removed by washing the plates 4 times. The detection Ab was added to each well. The plates were incubated at 4° C. overnight and the washing steps were repeated. After a 2 hour incubation with streptavidin-AP, the plates were washed. Aliquots (100 µl) of BCIP/NBT chromogen were added to each well to develop the spots. The reaction was stopped after 60 minutes by washing with water. The spots were scanned and counted with computer-assisted image analysis (Cellular Technology Ltd, Cleveland, Ohio). When experimental values were significantly different from the mean number of spots against non-pulsed T2 cells (background values), as determined by a two-tailed Wilcoxon rank sum test, the background values were subtracted from the experimental values. The coefficient of variation of intra-assay for ELISPOT in these experiments was less than 10%. The data are shown in FIG. 5 and FIG. 7.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising dendritic cells, wherein the dendritic cells present on human leukocyte antigen (HLA) on their surface peptide epitopes, wherein the peptide epitopes are each 9 to 13 amino acids length and comprise the following six amino acid sequences:

RSDSGQQARY from AIM-2; (SEQ ID NO: 3)

EADPTGHSY from MAGE-1; (SEQ ID NO: 4)

SVYDFFVWL from TRP-2; (SEQ ID NO: 5)

IMDQVPFSV, a superagonist peptide from gp100; (SEQ ID NO: 67)

VMAGVGSPYV from HER-2; (SEQ ID NO: 37)
and

WLPFGFILI from IL-13 receptor α2, (SEQ ID NO: 8)

wherein the dendritic cells acquired the peptide epitopes in vitro by exposure to synthetic peptides comprising the peptide epitopes.

2. The composition of claim 1, wherein the peptide epitopes comprise an HLA epitope from at least one antigen other than TRP-2, MAGE-1, HER-2, IL-13 receptor α2, gp100, and AIM2.

3. The composition of claim 1, wherein the composition comprises between $10^5$ and $10^8$ dendritic cells.

4. The composition of claim 1, wherein the composition comprises autologous dendritic cells.

5. The composition of claim 1, wherein the composition comprises allogeneic dendritic cells.

6. The composition of claim 1, wherein the dendritic cells present on HLA on their surface peptide epitopes of 9 or 10 amino acids in length.

7. The composition of claim 1, wherein the peptide epitopes consist of the following six amino acid sequences:

RSDSGQQARY from AIM-2; (SEQ ID NO: 3)

EADPTGHSY from MAGE-1; (SEQ ID NO: 4)

SVYDFFVWL from TRP-2; (SEQ ID NO: 5)

IMDQVPFSV, a superagonist peptide from gp100; (SEQ ID NO: 67)

VMAGVGSPYV from HER-2; (SEQ ID NO: 37)
and

WLPFGFILI from IL-13 receptor α2. (SEQ ID NO: 8)

8. A process comprising:
obtaining bone marrow derived mononuclear cells from a patient,
culturing the mononuclear cells in vitro under conditions in which mononuclear cells become adherent to a culture vessel,
selecting a subset of the mononuclear cells comprising adherent cells,
culturing the adherent cells in the presence of one or more cytokines under conditions in which the cells differentiate into antigen presenting cells,
culturing the antigen presenting cells in the presence of synthetic peptides of the following six antigens: TRP-2, MAGE-1, HER-2, IL-13 receptor α2, gp100, and AIM2, wherein the synthetic peptides are each 9 to 13 amino acids in length and comprise the following six amino acid sequences:

RSDSGQQARY from AIM-2; (SEQ ID NO: 3)

EADPTGHSY from MAGE-1; (SEQ ID NO: 4)

SVYDFFVWL from TRP-2; (SEQ ID NO: 5)

ITDQVPFSV, a superagonist peptide from gp100; (SEQ ID NO: 67)

KIFGSLAFL from HER-2; (SEQ ID NO: 37)
and

WLPFGFILI from IL-13 receptor α2, (SEQ ID NO: 8)

under conditions in which the antigen presenting cells present the peptides on human leukocyte antigen (HLA), wherein the antigen presenting cells are dendritic cells.

9. The process of claim 8, wherein the bone marrow derived cells are obtained from a patient with a glioma.

10. The process of claim 8, wherein the antigen presenting cells are cultured in the presence of a synthetic peptide from at least one antigen other than TRP-2, MAGE-1, HER-2, IL-13receptor α2, gp100, and AIM2.

* * * * *

UNITED STATES PATENT AND TRADEMARK OFFICE
CERTIFICATE OF CORRECTION

PATENT NO.        : 9,433,667 B2
APPLICATION NO.   : 13/327125
DATED             : September 6, 2016
INVENTOR(S)       : John S. Yu, Gentao Liu and Keith L. Black It is certified that error appears in the above-identified patent and that said Letters Patent is hereby corrected as shown below:

In the Claims

Claim 1
   Column 69, line 31, delete "from" and insert --of--.

Claim 7
   Column 70, line 17, delete "from" and insert --of--.

Claim 8
   Column 70, line 51, delete "ITDQVPFSV," and insert --IMDQVPFSV,--.
   Column 70, line 51, delete "from" and insert --of--.
   Column 70, line 54, delete "KIFGSLAFL" and insert --VMAGVGSPYV,--.

Claim 10
   Column 70, line 66, delete "IL-13receptor" and insert --IL-13 receptor--.

Signed and Sealed this
Twentieth Day of December, 2016

Michelle K. Lee
*Director of the United States Patent and Trademark Office*

SEQUENCE LISTING

```
<160> NUMBER OF SEQ ID NOS: 71

<210> SEQ ID NO 1
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 1

Arg Arg Ile Leu His Asn Gly Ala Tyr Ser Leu Arg Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 2

Arg Arg Lys Ile Phe Gly Ser Leu Ala Phe Leu Arg Arg
1               5                   10

<210> SEQ ID NO 3
<211> LENGTH: 10
<212> TYPE: PRT
<213> ORGANISM: Homo sapiens

<400> SEQUENCE: 3

Arg Ser Asp Ser Gly Gln Gln Ala Arg Tyr
1               5                   10

<210> SEQ ID NO 4
<211> LENGTH: 9
<212> TYPE: PRT
<213> ORGANISM: Homo sapiens

<400> SEQUENCE: 4

Glu Ala Asp Pro Thr Gly His Ser Tyr
1               5

<210> SEQ ID NO 5
<211> LENGTH: 9
<212> TYPE: PRT
<213> ORGANISM: Homo sapiens

<400> SEQUENCE: 5
```

```
Ser Val Tyr Asp Phe Phe Val Trp Leu
 1               5

<210> SEQ ID NO 6
<211> LENGTH: 9
<212> TYPE: PRT
<213> ORGANISM: Homo sapiens

<400> SEQUENCE: 6

Ile Thr Asp Gln Val Pro Phe Ser Val
 1               5

<210> SEQ ID NO 7
<211> LENGTH: 9
<212> TYPE: PRT
<213> ORGANISM: Homo sapiens

<400> SEQUENCE: 7

Lys Ile Phe Gly Ser Leu Ala Phe Leu
 1               5

<210> SEQ ID NO 8
<211> LENGTH: 9
<212> TYPE: PRT
<213> ORGANISM: Homo sapiens

<400> SEQUENCE: 8

Trp Leu Pro Phe Gly Phe Ile Leu Ile
 1               5

<210> SEQ ID NO 9
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 9

Arg Arg Arg Ser Asp Ser Gly Gln Gln Ala Arg Tyr Arg Arg
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 10

Arg Arg Glu Ala Asp Pro Thr Gly His Ser Tyr Arg Arg
 1               5                  10

<210> SEQ ID NO 11
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 11

Arg Arg Ser Val Tyr Asp Phe Phe Val Trp Leu Arg Arg
 1               5                  10

<210> SEQ ID NO 12
<211> LENGTH: 13
```

```
<212> TYPE: PRT
<213> ORGANISM: Artificial Sequence
<220> FEATURE:
<223> OTHER INFORMATION: Synthetically generated peptide

<400> SEQUENCE: 12

Arg Arg Ile Thr Asp Gln Val Pro Phe Ser Val Arg Arg
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 13

Arg Arg Trp Leu Pro Phe Gly Phe Ile Leu Ile Arg Arg
1               5                   10

<210> SEQ ID NO 14
<211> LENGTH: 75
<212> TYPE: PRT
<213> ORGANISM: Homo sapiens

<400> SEQUENCE: 14

Met Val Val Leu Gly Met Gln Thr Glu Glu Gly His Cys Ile Met Leu
1               5                   10                  15

Arg Gly Leu Ala Pro Ser Leu Gly Gly Thr Gln Val Ile Cys Lys Val
            20                  25                  30

Val Gly Leu Pro Ser Ser Ile Gly Phe Asn Thr Ser Ser His Leu Leu
        35                  40                  45

Phe Pro Ala Thr Leu Gln Gly Ala Pro Thr His Phe Pro Cys Arg Trp
    50                  55                  60

Arg Gln Gly Gly Ser Thr Asp Asn Pro Pro Ala
65                  70                  75

<210> SEQ ID NO 15
<211> LENGTH: 661
<212> TYPE: PRT
<213> ORGANISM: Homo sapiens

<400> SEQUENCE: 15

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
            85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
            115                 120                 125

Ala Cys Ile Phe Pro Asp Gly Gly Pro Cys Pro Ser Gly Ser Trp Ser
```

-continued

```
            130                 135                 140
Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
                180                 185                 190

Gly Ser Arg Ser Tyr Val Pro Leu Ala His Ser Ser Ala Phe Thr
                195                 200                 205

Ile Thr Asp Gln Val Pro Phe Ser Val Ser Val Ser Gln Leu Arg Ala
                210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
                260                 265                 270

Ala Leu Val Val Thr His Thr Tyr Leu Glu Pro Gly Pro Val Thr Ala
                275                 280                 285

Gln Val Val Leu Gln Ala Ala Ile Pro Leu Thr Ser Cys Gly Ser Ser
                290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
                340                 345                 350

Val Pro Thr Thr Glu Val Ile Ser Thr Ala Pro Val Gln Met Pro Thr
                355                 360                 365

Ala Glu Ser Thr Gly Met Thr Pro Glu Lys Val Pro Val Ser Glu Val
                370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
                420                 425                 430

Ile Pro Glu Pro Glu Gly Pro Asp Ala Ser Ser Ile Met Ser Thr Glu
                435                 440                 445

Ser Ile Thr Gly Ser Leu Gly Pro Leu Leu Asp Gly Thr Ala Thr Leu
450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
                500                 505                 510

Thr Val Ser Cys Gln Gly Gly Leu Pro Lys Glu Ala Cys Met Glu Ile
                515                 520                 525

Ser Ser Pro Gly Cys Gln Pro Pro Ala Gln Arg Leu Cys Gln Pro Val
                530                 535                 540

Leu Pro Ser Pro Ala Cys Gln Leu Val Leu His Gln Ile Leu Lys Gly
545                 550                 555                 560
```

```
Gly Ser Gly Thr Tyr Cys Leu Asn Val Ser Leu Ala Asp Thr Asn Ser
            565                 570                 575

Leu Ala Val Val Ser Thr Gln Leu Ile Met Pro Gln Glu Ala Gly
            580                 585                 590

Leu Gly Gln Val Pro Leu Ile Val Gly Ile Leu Leu Val Leu Met Ala
            595                 600                 605

Val Val Leu Ala Ser Leu Ile Tyr Arg Arg Arg Leu Met Lys Gln Asp
            610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
            645                 650                 655

Ser Gly Gln Gln Val
            660

<210> SEQ ID NO 16
<211> LENGTH: 1255
<212> TYPE: PRT
<213> ORGANISM: Homo sapiens

<400> SEQUENCE: 16

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
```

```
                260                 265                 270
Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685
```

-continued

```
Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
                1060                1065                1070

Ser Pro Leu Ala Pro Ser Glu Gly Ala Gly Ser Asp Val Phe Asp Gly
            1075                1080                1085

Asp Leu Gly Met Gly Ala Ala Lys Gly Leu Gln Ser Leu Pro Thr His
    1090                1095                1100
```

```
Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
            1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
            1155                1160                1165

Arg Pro Lys Thr Leu Ser Pro Gly Lys Asn Gly Val Val Lys Asp Val
            1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
            1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
            1235                1240                1245

Leu Gly Leu Asp Val Pro Val
            1250                1255

<210> SEQ ID NO 17
<211> LENGTH: 380
<212> TYPE: PRT
<213> ORGANISM: Homo sapiens

<400> SEQUENCE: 17

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
210                 215                 220
```

```
Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Cys Glu Ile Lys Leu
            245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
                275                 280                 285

Glu Asn Glu Thr Tyr Thr Leu Lys Thr Thr Asn Glu Thr Arg Gln Leu
            290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
                355                 360                 365

Tyr Pro Lys Met Ile Pro Glu Phe Phe Cys Asp Thr
370                 375                 380

<210> SEQ ID NO 18
<211> LENGTH: 309
<212> TYPE: PRT
<213> ORGANISM: Homo sapiens

<400> SEQUENCE: 18

Met Ser Leu Glu Gln Arg Ser Leu His Cys Lys Pro Glu Glu Ala Leu
1               5                   10                  15

Glu Ala Gln Gln Glu Ala Leu Gly Leu Val Cys Val Gln Ala Ala Thr
                20                  25                  30

Ser Ser Ser Ser Pro Leu Val Leu Gly Thr Leu Glu Glu Val Pro Thr
            35                  40                  45

Ala Gly Ser Thr Asp Pro Pro Gln Ser Pro Gln Gly Ala Ser Ala Phe
50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Pro Glu Ile Phe
130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
```

```
                        210                 215                 220
Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
                260                 265                 270

Glu Thr Ser Tyr Val Lys Val Leu Glu Tyr Val Ile Lys Val Ser Ala
                275                 280                 285

Arg Val Arg Phe Phe Phe Pro Ser Leu Arg Glu Ala Ala Leu Arg Glu
                290                 295                 300

Glu Glu Glu Gly Val
305

<210> SEQ ID NO 19
<211> LENGTH: 519
<212> TYPE: PRT
<213> ORGANISM: Homo sapiens

<400> SEQUENCE: 19

Met Ser Pro Leu Trp Trp Gly Phe Leu Leu Ser Cys Leu Gly Cys Lys
1               5                   10                  15

Ile Leu Pro Gly Ala Gln Gly Gln Phe Pro Arg Val Cys Met Thr Val
                20                  25                  30

Asp Ser Leu Val Asn Lys Glu Cys Cys Pro Arg Leu Gly Ala Glu Ser
            35                  40                  45

Ala Asn Val Cys Gly Ser Gln Gly Arg Gly Gln Cys Thr Glu Val
50                  55                  60

Arg Ala Asp Thr Arg Pro Trp Ser Gly Pro Tyr Ile Leu Arg Asn Gln
65                  70                  75                  80

Asp Asp Arg Glu Leu Trp Pro Arg Lys Phe Phe His Arg Thr Cys Lys
                85                  90                  95

Cys Thr Gly Asn Phe Ala Gly Tyr Asn Cys Gly Asp Cys Lys Phe Gly
                100                 105                 110

Trp Thr Gly Pro Asn Cys Glu Arg Lys Lys Pro Pro Val Ile Arg Gln
                115                 120                 125

Asn Ile His Ser Leu Ser Pro Gln Glu Arg Glu Gln Phe Leu Gly Ala
                130                 135                 140

Leu Asp Leu Ala Lys Lys Arg Val His Pro Asp Tyr Val Ile Thr Thr
145                 150                 155                 160

Gln His Trp Leu Gly Leu Leu Gly Pro Asn Gly Thr Gln Pro Gln Phe
                165                 170                 175

Ala Asn Cys Ser Val Tyr Asp Phe Phe Val Trp Leu His Tyr Tyr Ser
                180                 185                 190

Val Arg Asp Thr Leu Leu Gly Pro Gly Arg Pro Tyr Arg Ala Ile Asp
                195                 200                 205

Phe Ser His Gln Gly Pro Ala Phe Val Thr Trp His Arg Tyr His Leu
                210                 215                 220

Leu Cys Leu Glu Arg Asp Leu Gln Arg Leu Ile Gly Asn Glu Ser Phe
225                 230                 235                 240

Ala Leu Pro Tyr Trp Asn Phe Ala Thr Gly Arg Asn Glu Cys Asp Val
                245                 250                 255

Cys Thr Asp Gln Leu Phe Gly Ala Ala Arg Pro Asp Asp Pro Thr Leu
                260                 265                 270
```

```
Ile Ser Arg Asn Ser Arg Phe Ser Ser Trp Glu Thr Val Cys Asp Ser
            275                 280                 285

Leu Asp Asp Tyr Asn His Leu Val Thr Leu Cys Asn Gly Thr Tyr Glu
        290                 295                 300

Gly Leu Leu Arg Arg Asn Gln Met Gly Arg Asn Ser Met Lys Leu Pro
305                 310                 315                 320

Thr Leu Lys Asp Ile Arg Asp Cys Leu Ser Leu Gln Lys Phe Asp Asn
                325                 330                 335

Pro Pro Phe Phe Gln Asn Ser Thr Phe Ser Phe Arg Asn Ala Leu Glu
                340                 345                 350

Gly Phe Asp Lys Ala Asp Gly Thr Leu Asp Ser Gln Val Met Ser Leu
        355                 360                 365

His Asn Leu Val His Ser Phe Leu Asn Gly Thr Asn Ala Leu Pro His
    370                 375                 380

Ser Ala Ala Asn Asp Pro Ile Phe Val Val Leu His Ser Phe Thr Asp
385                 390                 395                 400

Ala Ile Phe Asp Glu Trp Met Lys Arg Phe Asn Pro Pro Ala Asp Ala
                405                 410                 415

Trp Pro Gln Glu Leu Ala Pro Ile Gly His Asn Arg Met Tyr Asn Met
                420                 425                 430

Val Pro Phe Phe Pro Pro Val Thr Asn Glu Glu Leu Phe Leu Thr Ser
        435                 440                 445

Asp Gln Leu Gly Tyr Ser Tyr Ala Ile Asp Leu Pro Val Ser Val Glu
    450                 455                 460

Glu Thr Pro Gly Trp Pro Thr Thr Leu Leu Val Val Met Gly Thr Leu
465                 470                 475                 480

Val Ala Leu Val Gly Leu Phe Val Leu Leu Ala Phe Leu Gln Tyr Arg
                485                 490                 495

Arg Leu Arg Lys Gly Tyr Thr Pro Leu Met Glu Thr His Leu Ser Ser
                500                 505                 510

Lys Arg Tyr Thr Glu Glu Ala
        515

<210> SEQ ID NO 20
<211> LENGTH: 8
<212> TYPE: PRT
<213> ORGANISM: Homo sapiens

<400> SEQUENCE: 20

Ser Asn Asp Gly Pro Thr Leu Ile
1               5

<210> SEQ ID NO 21
<211> LENGTH: 9
<212> TYPE: PRT
<213> ORGANISM: Homo sapiens

<400> SEQUENCE: 21

Lys Thr Trp Gly Gln Tyr Trp Gln Val
1               5

<210> SEQ ID NO 22
<211> LENGTH: 9
<212> TYPE: PRT
<213> ORGANISM: Homo sapiens

<400> SEQUENCE: 22

Tyr Leu Glu Pro Gly Pro Val Thr Ala
```

<210> SEQ ID NO 23
<211> LENGTH: 10
<212> TYPE: PRT
<213> ORGANISM: Homo sapiens

<400> SEQUENCE: 23

Ser Leu Ile Tyr Arg Arg Arg Leu Met Lys
1               5                   10

<210> SEQ ID NO 24
<211> LENGTH: 9
<212> TYPE: PRT
<213> ORGANISM: Homo sapiens

<400> SEQUENCE: 24

Leu Ile Tyr Arg Arg Arg Leu Met Lys
1               5

<210> SEQ ID NO 25
<211> LENGTH: 9
<212> TYPE: PRT
<213> ORGANISM: Homo sapiens

<400> SEQUENCE: 25

Arg Leu Met Lys Gln Asp Phe Ser Val
1               5

<210> SEQ ID NO 26
<211> LENGTH: 9
<212> TYPE: PRT
<213> ORGANISM: Homo sapiens

<400> SEQUENCE: 26

Arg Leu Pro Arg Ile Phe Cys Ser Cys
1               5

<210> SEQ ID NO 27
<211> LENGTH: 10
<212> TYPE: PRT
<213> ORGANISM: Homo sapiens

<400> SEQUENCE: 27

Val Leu Tyr Arg Tyr Gly Ser Phe Ser Val
1               5                   10

<210> SEQ ID NO 28
<211> LENGTH: 9
<212> TYPE: PRT
<213> ORGANISM: Homo sapiens

<400> SEQUENCE: 28

Ala Leu Cys Arg Trp Gly Leu Leu Leu
1               5

<210> SEQ ID NO 29
<211> LENGTH: 9
<212> TYPE: PRT
<213> ORGANISM: Homo sapiens

<400> SEQUENCE: 29

Arg Trp Gly Leu Leu Leu Ala Leu Leu
1               5

```
<210> SEQ ID NO 30
<211> LENGTH: 9
<212> TYPE: PRT
<213> ORGANISM: Homo sapiens

<400> SEQUENCE: 30

Thr Tyr Leu Pro Thr Asn Ala Ser Leu
1               5

<210> SEQ ID NO 31
<211> LENGTH: 9
<212> TYPE: PRT
<213> ORGANISM: Homo sapiens

<400> SEQUENCE: 31

Gln Leu Phe Glu Asp Asn Tyr Ala Leu
1               5

<210> SEQ ID NO 32
<211> LENGTH: 9
<212> TYPE: PRT
<213> ORGANISM: Homo sapiens

<400> SEQUENCE: 32

Ile Leu His Asn Gly Ala Tyr Ser Leu
1               5

<210> SEQ ID NO 33
<211> LENGTH: 9
<212> TYPE: PRT
<213> ORGANISM: Homo sapiens

<400> SEQUENCE: 33

Ile Ile Ser Ala Val Val Gly Ile Leu
1               5

<210> SEQ ID NO 34
<211> LENGTH: 9
<212> TYPE: PRT
<213> ORGANISM: Homo sapiens

<400> SEQUENCE: 34

Val Val Leu Gly Val Val Phe Gly Ile
1               5

<210> SEQ ID NO 35
<211> LENGTH: 9
<212> TYPE: PRT
<213> ORGANISM: Homo sapiens

<400> SEQUENCE: 35

Arg Leu Leu Gln Glu Thr Glu Leu Val
1               5

<210> SEQ ID NO 36
<211> LENGTH: 9
<212> TYPE: PRT
<213> ORGANISM: Homo sapiens

<400> SEQUENCE: 36

Val Leu Arg Glu Asn Thr Ser Pro Lys
1               5

<210> SEQ ID NO 37
```

```
<211> LENGTH: 10
<212> TYPE: PRT
<213> ORGANISM: Homo sapiens

<400> SEQUENCE: 37

Val Met Ala Gly Val Gly Ser Pro Tyr Val
 1               5                  10

<210> SEQ ID NO 38
<211> LENGTH: 9
<212> TYPE: PRT
<213> ORGANISM: Homo sapiens

<400> SEQUENCE: 38

Pro Tyr Val Ser Arg Leu Leu Gly Ile
 1               5

<210> SEQ ID NO 39
<211> LENGTH: 9
<212> TYPE: PRT
<213> ORGANISM: Homo sapiens

<400> SEQUENCE: 39

Cys Leu Thr Ser Thr Val Gln Leu Val
 1               5

<210> SEQ ID NO 40
<211> LENGTH: 9
<212> TYPE: PRT
<213> ORGANISM: Homo sapiens

<400> SEQUENCE: 40

Gln Leu Met Pro Tyr Gly Cys Leu Leu
 1               5

<210> SEQ ID NO 41
<211> LENGTH: 8
<212> TYPE: PRT
<213> ORGANISM: Homo sapiens

<400> SEQUENCE: 41

Tyr Leu Glu Asp Val Arg Leu Val
 1               5

<210> SEQ ID NO 42
<211> LENGTH: 9
<212> TYPE: PRT
<213> ORGANISM: Homo sapiens

<400> SEQUENCE: 42

Val Leu Val Lys Ser Pro Asn His Val
 1               5

<210> SEQ ID NO 43
<211> LENGTH: 17
<212> TYPE: PRT
<213> ORGANISM: Homo sapiens

<400> SEQUENCE: 43

Lys Val Pro Ile Lys Trp Met Ala Leu Glu Ser Ile Leu Arg Arg Arg
 1               5                  10                  15

Phe

<210> SEQ ID NO 44
```

```
<211> LENGTH: 10
<212> TYPE: PRT
<213> ORGANISM: Homo sapiens

<400> SEQUENCE: 44

Tyr Met Ile Met Val Lys Cys Trp Met Ile
1               5                   10

<210> SEQ ID NO 45
<211> LENGTH: 9
<212> TYPE: PRT
<213> ORGANISM: Homo sapiens

<400> SEQUENCE: 45

Glu Leu Val Ser Glu Phe Ser Arg Met
1               5

<210> SEQ ID NO 46
<211> LENGTH: 11
<212> TYPE: PRT
<213> ORGANISM: Homo sapiens

<400> SEQUENCE: 46

Ile Thr Lys Lys Val Ala Asp Leu Val Gly Phe
1               5                   10

<210> SEQ ID NO 47
<211> LENGTH: 9
<212> TYPE: PRT
<213> ORGANISM: Homo sapiens

<400> SEQUENCE: 47

Asn Tyr Lys His Cys Phe Pro Glu Ile
1               5

<210> SEQ ID NO 48
<211> LENGTH: 10
<212> TYPE: PRT
<213> ORGANISM: Homo sapiens

<400> SEQUENCE: 48

Lys Glu Ala Asp Pro Thr Gly His Ser Tyr
1               5                   10

<210> SEQ ID NO 49
<211> LENGTH: 9
<212> TYPE: PRT
<213> ORGANISM: Homo sapiens

<400> SEQUENCE: 49

Ser Ala Tyr Gly Glu Pro Arg Lys Leu
1               5

<210> SEQ ID NO 50
<211> LENGTH: 9
<212> TYPE: PRT
<213> ORGANISM: Homo sapiens

<400> SEQUENCE: 50

Lys Val Leu Glu Tyr Val Ile Lys Val
1               5

<210> SEQ ID NO 51
<211> LENGTH: 9
<212> TYPE: PRT
```

<213> ORGANISM: Homo sapiens

<400> SEQUENCE: 51

Leu Leu Gly Pro Gly Arg Pro Tyr Arg
 1               5

<210> SEQ ID NO 52
<211> LENGTH: 10
<212> TYPE: PRT
<213> ORGANISM: Homo sapiens

<400> SEQUENCE: 52

Glu Val Ile Ser Cys Lys Leu Ile Lys Arg
 1               5                  10

<210> SEQ ID NO 53
<211> LENGTH: 9
<212> TYPE: PRT
<213> ORGANISM: Homo sapiens

<400> SEQUENCE: 53

Ser Leu Asp Asp Tyr Asn His Leu Val
 1               5

<210> SEQ ID NO 54
<211> LENGTH: 9
<212> TYPE: PRT
<213> ORGANISM: Homo sapiens

<400> SEQUENCE: 54

Thr Leu Asp Ser Gln Val Met Ser Leu
 1               5

<210> SEQ ID NO 55
<211> LENGTH: 9
<212> TYPE: PRT
<213> ORGANISM: Homo sapiens

<400> SEQUENCE: 55

Ala Asn Asp Pro Ile Phe Val Val Leu
 1               5

<210> SEQ ID NO 56
<211> LENGTH: 9
<212> TYPE: PRT
<213> ORGANISM: Homo sapiens

<400> SEQUENCE: 56

Leu Leu Tyr Asn Ala Thr Thr Asn Ile
 1               5

<210> SEQ ID NO 57
<211> LENGTH: 7
<212> TYPE: PRT
<213> ORGANISM: Homo sapiens

<400> SEQUENCE: 57

Ala Thr Thr Asn Ile His Tyr
 1               5

<210> SEQ ID NO 58
<211> LENGTH: 8
<212> TYPE: PRT
<213> ORGANISM: Homo sapiens

```
<400> SEQUENCE: 58

Asn Ala Thr Thr Asn Ile His Val
1               5

<210> SEQ ID NO 59
<211> LENGTH: 9
<212> TYPE: PRT
<213> ORGANISM: Homo sapiens

<400> SEQUENCE: 59

Tyr Ala Ile Asp Leu Pro Val Ser Val
1               5

<210> SEQ ID NO 60
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 60

Arg Arg Gly Tyr Tyr Gly Val Ser Leu Ala Asp Trp Val Cys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 61

Gly Tyr Tyr Gly Val Ser Leu Ala Asp Trp Val Cys Arg Arg
1               5                   10

<210> SEQ ID NO 62
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 62

Arg Arg Gly Tyr Tyr Gly Val Ser Leu Ala Asp Trp Val Cys Arg Arg
1               5                   10                  15

<210> SEQ ID NO 63
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 63

Phe Leu Asp Gln Val Pro Tyr Ser Val
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 64

Phe Met Asp Gln Val Pro Tyr Ser Val
```

```
<210> SEQ ID NO 65
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 65

Tyr Met Asp Gln Val Pro Tyr Ser Val
 1               5

<210> SEQ ID NO 66
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 66

Ile Leu Asp Gln Val Pro Phe Ser Val
 1               5

<210> SEQ ID NO 67
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 67

Ile Met Asp Gln Val Pro Phe Ser Val
 1               5

<210> SEQ ID NO 68
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 68

Phe Met Ala Asn Val Ala Ile Pro His Leu
 1               5                  10

<210> SEQ ID NO 69
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 69

Phe Met His Asn Val Pro Ile Pro Tyr Leu
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 70

Phe Tyr Ala Asn Val Pro Ser Pro His Leu
 1               5                  10
```

```
<210> SEQ ID NO 71
<211> LENGTH: 10
<212> TYPE: PRT
<213> ORGANISM: Homo sapiens

<400> SEQUENCE: 71

Val Met Ala Gly Val Gly Ser Pro Tyr Val
1               5                   10
```